(12) United States Patent
Jermy et al.

(10) Patent No.: US 11,857,639 B2
(45) Date of Patent: *Jan. 2, 2024

(54) METHOD FOR TREATING BREAST CANCER

(71) Applicant: Imam Abdulrahman Bin Faisal University, Dammam (SA)

(72) Inventors: B. Rabindran Jermy, Dammam (SA); Vijaya Ravinayagam, Dammam (SA); Dana Almohazey, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,842

(22) Filed: Aug. 16, 2023

(65) Prior Publication Data

US 2023/0390415 A1 Dec. 7, 2023

Related U.S. Application Data

(63) Continuation of application No. 17/351,758, filed on Jun. 18, 2021, now Pat. No. 11,779,652.

(51) Int. Cl.
| | |
|---|---|
| *A61K 47/69* | (2017.01) |
| *A61K 33/243* | (2019.01) |
| *A61K 31/282* | (2006.01) |
| *A61K 47/10* | (2017.01) |
| *A61K 31/138* | (2006.01) |
| *B82Y 25/00* | (2011.01) |
| *B82Y 30/00* | (2011.01) |
| *B82Y 40/00* | (2011.01) |
| *B82Y 5/00* | (2011.01) |

(52) U.S. Cl.
CPC ........ *A61K 47/6923* (2017.08); *A61K 31/138* (2013.01); *A61K 31/282* (2013.01); *A61K 33/243* (2019.01); *A61K 47/10* (2013.01); *A61K 2121/00* (2013.01); *A61K 2800/47* (2013.01); *B82Y 5/00* (2013.01); *B82Y 25/00* (2013.01); *B82Y 30/00* (2013.01); *B82Y 40/00* (2013.01)

(58) Field of Classification Search
CPC .............. A61K 47/6923; A61K 33/243; A61K 31/138; A61K 31/282; A61K 47/10; A61K 2800/47; B82Y 5/00; B82Y 25/00; B82Y 30/00; B82Y 40/00
See application file for complete search history.

(56) References Cited

U.S. PATENT DOCUMENTS

| | | | |
|---|---|---|---|
| 2014/0212479 A1 | 7/2014 | Zeinelden | |
| 2018/0280303 A1* | 10/2018 | Jermy | ................. B01J 20/3057 |
| 2019/0231897 A1 | 8/2019 | Balasamy et al. | |
| 2020/0038525 A1* | 2/2020 | Jermy | ................ A61K 47/6923 |
| 2020/0155480 A1 | 5/2020 | Ravinayagam et al. | |
| 2020/0281864 A1 | 9/2020 | Jermy et al. | |
| 2020/0338122 A1 | 10/2020 | Jermy et al. | |

FOREIGN PATENT DOCUMENTS

| | | |
|---|---|---|
| CN | 103464093 A | 12/2013 |
| CN | 104225599 A | 12/2014 |
| CN | 109529060 A | 3/2019 |
| CN | 109950014 A | 6/2019 |
| WO | WO 2019/122124 A1 | 6/2019 |

OTHER PUBLICATIONS

B. Zhou et al., "Curcumin increases breast cancer cell sensitivity to cisplatin by decreasing FEN1 expression," in Oncotarget, 2018, vol. 9, No. 13, pp. 11268-11278. (Year: 2018).*
Huitao Fan, et al., "A fibrous morphology silica-CoFe$_2$O$_4$ nanocarrier for anti-cancer drug delivery", Ceramics International, vol. 44, Issue 2, Feb. 1, 2018, pp. 2345-2350 (Abstract only).
Banalata Sahoo, et al., "Biocompatible mesoporous silica-coated superparamagnetic manganese ferrite nanoparticles for targeted drug delivery and MR imaging applications", Journal of Colloid and Interface Science, vol. 431, 2014, pp. 31-41.
Mahsa Asgari, et al., "A novel method for in situ encapsulation of curcumin in magnetite-silica core-shell nanocomposites: A multifunctional platform for controlled drug delivery and magnetic hyperthermia therapy", Journal of Molecular Liquids, vol. 324, Feb. 15, 2020, p. 114731 (Abstract only).
B. Rabindran Jermy, et al., "Hierarchical mesosilicalite nanoformulation integrated with cisplatin exhibits target-specific efficient anticancer activity", Applied Nanoscience, vol. 8, Apr. 26, 2018, pp. 1205-1220.
Vijaya Ravinayagam, et al., "Studying the loading effect of acidic type antioxidant on amorphous silica nanoparticle carriers", Journal of Nanoparticle Research, vol. 19, Article No. 190, May 27, 2017, pp. 1-14.
Zhou et al., "Curcumin increases breast cancer cell sensitivity to cisplatin by decreasing FEN 1 expression," in Oncotarget, 2018, vol. 9, No. 13, pp. 11268-11278. (Year: 2018).

* cited by examiner

*Primary Examiner* — Blessing M Fubara

(74) *Attorney, Agent, or Firm* — Oblon, McClelland, Maier & Neustadt, L.L.P.

(57) ABSTRACT

A nanomedicinal composition comprising a nanocarrier and a pharmaceutical agent mixture comprising an anti-cancer therapeutic and an antioxidant. The nanocarrier comprises a porous silicate matrix and particles of a magnetic ferrite disposed in the pores of the porous silicate matrix. The pharmaceutical agent mixture is disposed in the pores and/or on the surface of the nanocarrier by a solution phase impregnation process. The nanomedicinal composition is used in a method of treating breast cancer.

10 Claims, 10 Drawing Sheets

METHOD FOR TREATING BREAST CANCER

CROSS-REFERENCE TO RELATED APPLICATIONS

The present application is a Continuation of U.S. application Ser. No. 17/351,758, now allowed, having a filing date of Jun. 18, 2021.

BACKGROUND OF THE INVENTION

Field of the Invention

The present disclosure relates to a nanomedicinal composition comprising a nanocarrier, which comprises a porous silicate matrix and particles of a magnetic ferrite disposed in the pores of the porous silicate matrix, and a pharmaceutical agent mixture comprising an anti-cancer therapeutic and an antioxidant disposed in the pores and/or on the surface of the nanocarrier, as well as a method of making the nanomedicinal composition and a method of treating breast cancer using the nanomedicinal composition.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Chemotherapeutic treatment of cancer requires delivery of sufficient doses of an appropriate drug to the tumor, which often leads to resistance to the chemotherapy [Bruix J, & Llovet J M, Hepatology. 2002, 35, 3, 519-24, incorporated herein by reference in its entirety]. In recent years, the development of medicine and nanotechnology (nanomedicine) has broadened the scope for effective and efficient therapies for deadly diseases such as cancer. The available nanotherapeutics overcome the limitations of current drug therapy (conventional), namely untargeted drug release, low bioavailability, and low therapeutic index. Nanobiotechnology research has been rising steadily in interdisciplinary core area for the development of targeted drug delivery system. The most striking features of nanotherapeutics is the ability of nanoparticles to accommodate several components into its nano structure to generate multifunctional modality. Several nanocarriers based on hydrogels, alginate, clay, liposomes and polymeric species based therapeutic tools has been reported for treating chronic diseases such as cancer, cardiovascular and diabetics [Li, C., et. al., Acta Pharmaceutica Sinica. 2019, B 9, 1145-1162; Mantha, S., et. al., Mater. 2019, 12, 3323; Abduljauwad, S. N. & Ahmed, H., Sci Rep. 2019, 9, 5935; and de Lima, H. H. C., et. al., Carbohydrate Polymers 2018, 196, 126-134]. Hexagonal structured silica MCM-41 has found uses in catalysis, drug delivery support and gas adsorption as a result of interesting textural features such as a large surface area (greater than 1000 $m^2/g$), designable pore sizes (1.5-10 nm) and ordered nanochannels [Beck, J. S., et. al., J. Am. Chem. Soc. 1992, 114(27), 10834-10843; and Lanzafame, P., et. al., Micropor. Mesopor. Mater. 2020, 300, 110157]. Henceforth, MCM-41 has been exhaustively used in fine chemical synthesis and recently also reported for drug delivery applications [Chen, Y., et. al., Int. J. Nanomed. 2020, 15, 3099-3120]. Though MCM-41 based nanoformulations are reported, the presence of an amorphous framework decreases the stability of the hexagonal structure and increases the possibility of structural disintegration inside the body under acidic conditions. Various techniques have been applied to improve the hexagonal pore stability by preparing MCM-41 using zeolite fragments/seed solution [Vijaya Ravinayagam & Rabindran Jermy, B, J. Saudi Chem. Soc. 2019, 23 461-476]. Such MCM-41 hybrid material is considered to be the most stable because it combines the advantage of micropore zeolites stability and mesopore size of mesoporous materials. For instance, the synthesis and catalytic applications of hierarchical micro/mesoporous MCM-41 in petrochemistry was reported in 2012 [Odedairo, T., Balasamy, R. J., & Al-Khattaf, S., Catal. Sci. Technol. 2012, 2, 1275-1286]. The improved stability of MCM-41 was attributed to the presence of nano zeolitic seeds (primary or secondary zeolitic building units) in the synthesis gel which increases the framework crystallinity [Rabindran Jermy, B., & Vijaya Ravinayagam, Adv. Natural Sci. Nanosci. Nanotechnol. 2019, 10, 045003].

Cancer treatment using combination drugs is an attractive option to prevent drug resistance. Biopolymer Xylan, a polysaccharide modified with a redox sensitive conjugate disulfide linker has been reported for curcumin and 5-fluorouracil in cancer therapy. The dual delivery of drugs was shown to significantly inhibit the colon carcinoma cells HT-29 and HCT-15 [Sauraj, V., et. al., Mater. Sci. Engg C. 2020, 107, 110356]. Biocompatible polymers involving polyethylene glycol and poly(lactic-co-glycolic acid) tends to exhibit a superior release of antineoplastic drug (7-Ethyl-10-hydroxycamptothecin) and curcumin. The nanocomposite formulation with hydrophobic coating (dioeoylphosphatidic acid) has shown significant anticancer effect in human cervical HeLa and Ovarian cells [Li, X., & Gao, Y., Process Biochem. 2020, 98, 254-261]. Layer by layer deposition of natural polysaccharide chitosan and negatively charged dextran sulfate has been reported using double emulsion cross linking technique. Chitosan-Paclitaxel was prepared using interna oil in water emulsion. After addition of external water to oil emulsion, dextran sodium and chitosan bound 5-Fluorouracil was added and following lyophilized. The dual drug loaded nanoparticles with particle diameter of about 292 nm was reported to induce high inhibition of HepG2 cells [Wang, F., et. al., Colloids and Surfaces B: Biointerfaces. 2020, 190, 110925]. A bilayer structured vesicle Niosome functionalized with folic acid was found to be effective for dual drug carrier of curcumin and letrozole. Non-ionic surfactant Span 80 and chloestrol (lipid) to drug ratio optimization resulted in high dual drug encapsulation. The synergism between both drugs was observed to inhibit breast cancer cells (MCF-7 and MD-MB-231) leading to down regulation of genes Bc12, cyclin D and cyclin E genes and upregulate the p53, Bax, caspase-3 and caspase-9 genes [Akbarzadeh, I., et. al., Adv. Powder Technol. 2020, 31(9), 4064-4071].

In view of the foregoing, an objective of the present invention is to provide a nanomedicinal composition comprising a nanocarrier and a pharmaceutical agent mixture comprising an anti-cancer therapeutic and an antioxidant which are disposed within pores and/or on the surface of the nanocarrier. The nanocarrier incorporates a porous silicate matrix and particles of a magnetic ferrite. The magnetic properties may be useful for targeting, imaging, or triggering release from the nanocarrier.

SUMMARY OF THE INVENTION

The present disclosure relates to a nanomedicinal composition comprising a nanocarrier and a pharmaceutical agent mixture comprising an anti-cancer therapeutic and an antioxidant. The nanocarrier comprises a porous silicate matrix and particles of a magnetic ferrite of formula $MFe_2O_4$ disposed in the pores of the porous silicate matrix, where M is at least one transition metal selected from the group consisting of Cu, Ni, Co, and Mn. The pharmaceutical agent mixture is disposed in the pores and/or on the surface of the nanocarrier.

In some embodiments, the porous silicate matrix is at least one selected from the group consisting of MCM-41 and mesosilicalite.

In some embodiments, the porous silicate matrix is present in the form of particles having a mean particle size of 25 to 500 nm.

In some embodiments, the magnetic ferrite is copper ferrite of formula $CuFe_2O_4$.

In some embodiments, the magnetic ferrite is present in an amount of 15 to 45 wt % based on a total weight of the nanocarrier.

In some embodiments, the magnetic ferrite has a mean particle size of 5 to 50 nm.

In some embodiments, the anti-cancer therapeutic comprises a platinum (II) complex.

In some embodiments, the platinum (II) complex is at least one selected from the group consisting of cisplatin, carboplatin, and oxaliplatin.

In some embodiments, the platinum (II) complex is cisplatin.

In some embodiments, the anti-cancer therapeutic comprises tamoxifen.

In some embodiments, the antioxidant is at least one selected from the group consisting of quercetin, rutin, coenzyme Q10, gallic acid, and curcumin.

In some embodiments, the antioxidant is curcumin.

In some embodiments, a weight ratio of the antioxidant to the anti-cancer therapeutic is 1:1 to 10:1.

In some embodiments, the pharmaceutical agent mixture is present in the nanomedicinal composition in an amount of 5 to 50 wt %, based on a total weight of nanomedicinal composition.

The present disclosure also relates to a method of forming the nanomedicinal composition, the method comprising mixing an M(II) salt and a Fe(III) salt with the porous silicate matrix to form a powdery mixture, calcining the powdery mixture to form the nanocarrier, mixing the nanocarrier and the anti-cancer therapeutic in an aqueous solution thereby forming a therapeutic-containing nanocarrier, and mixing the therapeutic-containing nanocarrier and the antioxidant in an impregnation solution thereby forming the nanomedicinal composition.

In some embodiments, the calcining is performed at a temperature of 700 to 1,000° C.

In some embodiments, the aqueous solution is a saline, the anti-cancer therapeutic is present in the aqueous solution at a concentration of 1.0 to 20.0 mM, and the nanocarrier is present in the aqueous solution at a concentration of 20 to 100 mg/mL.

In some embodiments, the impregnation solution comprises an alcohol solvent, the antioxidant is present in the impregnation solution at a concentration of 1.0 to 20.0 mM, and the therapeutic-containing nanocarrier is present in the impregnation solution at a concentration of 2 to 30 mg/mL.

The present disclosure also relates to a method for treating breast cancer in a subject, the method comprising administering to a subject in need of therapy a pharmaceutical composition comprising the nanomedicinal composition.

In some embodiments, the method further comprises exposing the subject to an alternating magnetic field, thereby raising the temperature of the nanomedicinal composition.

BRIEF DESCRIPTION OF THE DRAWINGS

FIG. 8A is for MCF7 cells and FIG. 8B is for HFF cells;

FIGS. 9A-9D are for MCF7 cells and FIGS. 9E-9H are for HFF cells;

DETAILED DESCRIPTION OF THE INVENTION

Figure 1A:
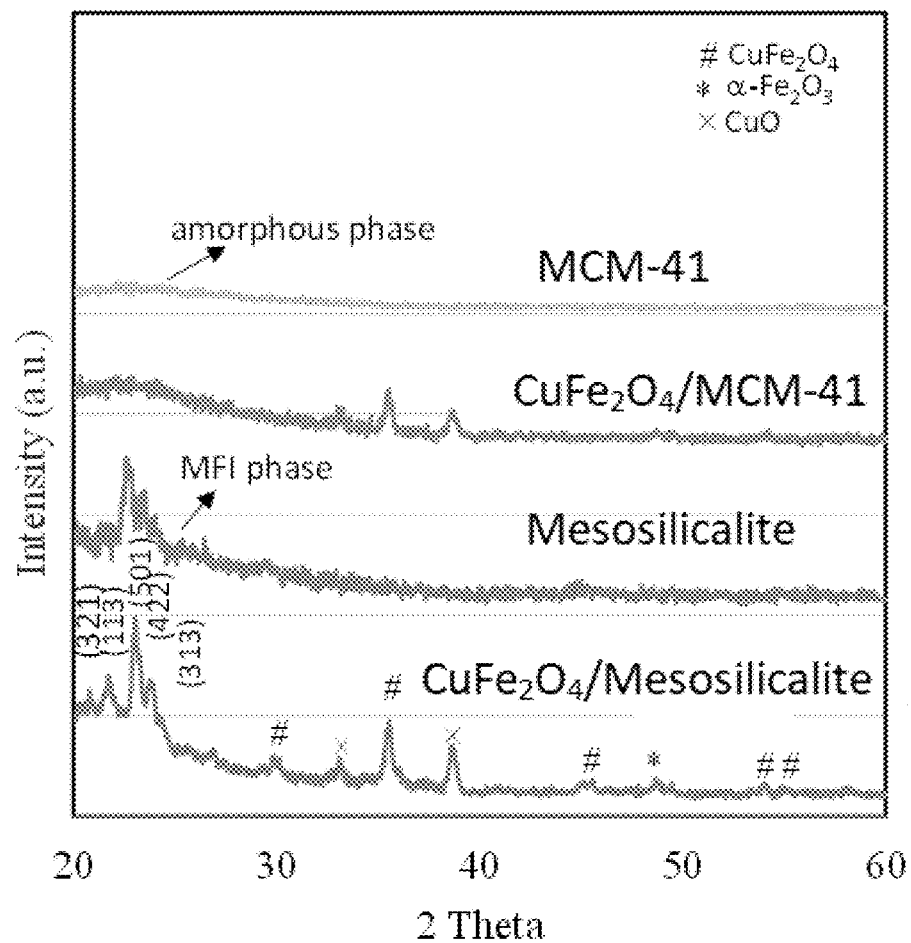
FIG. 1A shows X-ray diffraction patterns of MCM-41, $CuFe_2O_4$/MCM-41, Mesosilicalite, and $CuFe_2O_4$/Mesosilicalite.

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" mean that the subsequently described event(s) can or cannot occur or the subsequently described component(s) may or may not be present (e.g., 0 wt. %).

According to a first aspect, the present disclosure relates to a nanomedicinal composition comprising a nanocarrier and a pharmaceutical agent mixture comprising an anticancer therapeutic and an antioxidant. The nanocarrier comprises a porous silicate matrix and particles of a magnetic ferrite of formula $MFe_2O_4$ disposed in the pores of the porous silicate matrix, where M is at least one transition metal selected from the group consisting of Cu, Ni, Co, and Mn. The pharmaceutical agent mixture is disposed in the pores of and/or on a surface of the nanocarrier.

In general, any suitable porous silicate matrix known to one of ordinary skill in the art may be used in the nanomedicinal composition. Examples of such suitable porous silica, silicate, or aluminosilicate materials include, but are not limited to, MCM-41, MCM-48, Q-10 silica, hydrophobic silica, mesobeta, mesoZSM-5, SBA-15, KIT-5, KIT-6, mesosilicalite, hierarchical porous silicalite, and SBA-16. For the purposes of this disclosure, "silicate matrix" also includes aluminum-containing silicate materials. Such materials may be known as or referred to as aluminosilicates. Further, the term "silicate matrix" should be understood to include silica itself. Methods of obtaining the various types porous silica, silicate, or aluminosilicate material are well-known in the art [see for example Gobin, Oliver Christian "SBA-16 Materials: Synthesis, Diffusion, and Sorption Properties" Dissertation, Laval University, Ste-Foy, Quebec, Canada, January 2006, in particular section 2.2; and U.S. patent application Ser. No. 15/478,794—both incorporated herein by reference in their entireties].

In some embodiments, the porous silicate matrix is present in an amount of 55 to 85 wt %, preferably 57.5 to 82.5 wt %, preferably 60 to 80 wt %, preferably 62.5 to 77.5 wt %, preferably to 75 wt %, preferably 67.5 to 72.5 wt %, preferably 69 to 71 wt %, preferably 70 wt %, based on a total weight of the nanocarrier.

In some embodiments, the porous silicate matrix is at least one selected from the group consisting of MCM-41 and mesosilicalite.

MCM-41 (Mobil Composition of Matter No. 41) is a mesoporous silica material with a hierarchical structure from a family of silicate and aluminosilicate solids that were developed by researchers at Mobil Oil Corporation and that can be used as catalysts or catalyst supports. MCM-41 and MCM-48 both comprise an amorphous silica wall and possess long range ordered framework with uniform mesopores. These materials also possess large surface area, which can be up to more than 1,000 $m^2\ g^{-1}$. The pore diameter of these materials can be controlled to fall within a mesoporous range between 1.5 and 20 nm by adjusting the synthesis conditions and/or by employing surfactants with different chain lengths in their preparation. In embodiments where the porous silicate matrix is MCM-41, the nanocarrier may be referred to as a "MCM-41 nanocarrier".

Silicalite is a polymorph of silica having a structure analogous to zeolite. The term "mesosilicalite" may be used to refer to any silicalite material which contains mesopores. The term "hierarchical silicalite" is used to indicate a silicalite which has at least two types of pore systems with different pore size ranges. For example, a hierarchical silicalite may have a pore size range in the micropore range and a pore size range in the mesopore range. Such a material may be classified as both a mesosilicalite and a hierarchical silicalite. In some embodiments, the hierarchical silicalite includes mesopores of a hexagonal structure and micropores. In some embodiments, the micropores have a microporous volume in the range of 0.05 cc/g to 0.1 cc/g, cc/g to 0.09 cc/g, or 0.07 cc/g to 0.08 cc/g. U.S. patent application Ser. No. 15/478,794 which published as US 2018/0280303—incorporated herein by reference in its entirety, discloses the synthesis of an exemplary silicalite having a particle size in the range of 1-5 nm using Ludox AS-40 and tetrapropylammonium bromide (TPABr) as silica and templating agent, respectively. In embodiments where the porous silicate matrix is mesosilicalite, the nanocarrier may be referred to as a "mesosilicalite nanocarrier".

The hexagonal structure of mesosilicalite may be described as well-ordered and comparable in structure to MCM-41 mesoporous material as described by Kresge et al. (1992), Sayari, et al. (1996), and Moller, et al. (2013) [Kresge C T, Leonowicz M E, Roth W J, Vartuli J C, Beck J S, Nature 359 (1992)710-712; 15; A. Sayari, Chem. Mater. 8 (1996) 1840-1852; and K. Moller, T. Bein, Chem. Soc. Rev., 42 (2013) 3689, each incorporated herein in their entirety]. In some embodiments, the mesopores and micropores for the porous silicate matrix characterize the hierarchical structure of the silicalite, wherein the mesopores form the mesophase and the micropores form the microphase. The relative weight ratios of these two phases approximate the relative weight ratios of the SiMCM-41 and silicalite used in the synthesis.

In some embodiments, the hierarchy of the mesophase and microphase in hierarchical silicalite results in improved interaction with materials that can be carried, adsorbed, absorbed and/or otherwise contacted by the porous silicate matrix due to a greater surface area of contact with two phases instead of one phase, and an improved flow, or exchange, of the materials that may be carried into and out of the porous silicate matrix. The presence of micropores and mesopores in the porous silicate matrix may exhibit a unique hysteresis pattern. The pore size distribution of the silicalite typically exhibits two types of pores between 2.4 nm and 3.7 nm, while Q-10 silica and SiMCM-41 each show one type of pore at 15 nm and 2.9 nm, respectively.

The porous silicate matrix may comprise two types of materials, a first material having 2D properties and a second material having 3D properties. The first material may be layered under the second material, thus forming a hierarchically structured nanocarrier. In some such embodiments, the amount of mesophase and microphase is calculated based on the weight percentage of composite SiMCM-41/silicalite in comparison to parent silicalite and SiMCM-41. Alternatively, a calibration curve may be constructed from the X-Ray diffraction spectra of mesosilicalite nanocarriers synthesized from different amounts of parent silicalite and SiMCM-41. Then, the amount of mesophase and microphase may be determined from an X-Ray diffraction measurement.

In some embodiments of the mesosilicalite nanocarrier, the mesopores are ordered. The ordered structure of the mesopores may be a result of a template employed in the process of preparing the mesosilicalite nanocarrier, described further herein. The template, for example a tetrapropylammonium hydroxide, may assist colloidal silica, described further in the method of preparing the mesosilicalite nanocarrier, to self-order in formation of cylindrical pores which form the hexagonal structure. The ordered structure may allow for improved diffusion of materials into and out of the nanocarrier. This characteristic may make the nanocarriers useful as drug delivery agents.

In a preferred embodiment, the porous silicate matrix has a surface area in the range 300 m$^2$/g to 1400 m$^2$/g, more preferably in the range 400 m$^2$/g to 1200 m$^2$/g, and most preferably in the range of 600 m$^2$/g to 1000 m$^2$/g. The preferred porous silicate matrix has at least one type of pores with a diameter in the range of 1 nm to 60 nm, preferably in the range of 1.5 nm to 30 nm, more preferably in the range 2 nm to 10 nm, and most preferably in the range of 3 nm to 7 nm. Also, the preferred porous silicate matrix has a pore volume in the range of 0.11 cc/g to 1.5 cc/g, preferably in the range of 0.15 cc/g to 1.25 cc/g, more preferably in the range of 0.25 cc/g to 1 cc/g, and most preferably in the range of 0.5 cc/g to 0.75 cc/g.

In some embodiments, the porous silicate matrix is present in the form of particles. In general, the porous silicate matrix particles can be any shape known to one of ordinary skill in the art. Examples of suitable shapes the porous silicate matrix particles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, blocks, flakes, discs, granules, angular chunks, and mixtures thereof. Nanorods or nanowires are not a shape that the porous silicate matrix particles are envisioned as having in any embodiments.

In some embodiments, the porous silicate matrix particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of porous silicate matrix particles having a different shape. As used herein, the term "non-uniform shape" refers to an average consistent shape that differs by more than 10% of the distribution of porous silicate matrix particles having a different shape. In one embodiment, the shape is uniform and at least 90% of the porous silicate matrix particles are spherical or substantially circular, and less than 10% are polygonal. In another embodiment, the shape is non-uniform and less than 90% of the porous silicate matrix particles are spherical or substantially circular, and greater than 10% are polygonal.

In some embodiments, the porous silicate matrix particles have a mean particle size of 25 to 500 nm, preferably 30 to 450 nm, preferably 40 to 400 nm, preferably 50 to 350 nm, preferably 60 to 300 nm, preferably 70 to 250 nm. In embodiments where the porous silicate matrix particles are spherical, the particle size may refer to a particle diameter. In embodiments where the porous silicate matrix particles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the porous silicate matrix particles have an anisotropic shape such as nanorods, the particle size may refer to a length of the nanorod, a width of the nanorod, or an average of the length and width of the nanorod. In some embodiments, the particle size refers to the diameter of a sphere having an equivalent volume as the particle.

In some embodiments, the porous silicate matrix particles are monodisperse, having a coefficient of variation or relative standard deviation, expressed as a percentage and defined as the ratio of the particle size standard deviation (a) to the particle size mean (0 multiplied by 100 of less than 25%, preferably less than 10%, preferably less than 8%, preferably less than 6%, preferably less than 5%, preferably less than 4%, preferably less than 3%, preferably less than 2%. In some embodiments, the porous silicate matrix particles of the present disclosure are monodisperse having a particle size distribution ranging from 80% of the average particle size to 120% of the average particle size, preferably 90-110%, preferably 95-105% of the average particle size. In some embodiments, the porous silicate matrix particles are not monodisperse.

The nanocarrier also comprises particles of a magnetic ferrite of formula MFe$_2$O$_4$ disposed in the pores of the porous silicate matrix, where M is at least one transition metal selected from the group consisting of Cu, Ni, Co, and Mn. In some embodiments, the magnetic ferrite is a mixed metal or doped metal ferrite of formula M$_{1-x}$A$_x$Fe$_2$O$_4$, where A represents a transition metal or rare earth element and 0<x≤0.5. Examples of such mixed meal or doped metal ferrites include Mn$_{0.5}$Zn$_{0.5}$Fe$_2$O$_4$ (also represented as (MnZn)Fe$_2$O$_4$), Mn$_{0.9}$Ce$_{0.1}$Fe$_2$O$_4$, and Mn$_{0.9}$Co$_{0.1}$Fe$_2$O$_4$. In preferred embodiments, the magnetic ferrite is copper ferrite of formula CuFe$_2$O$_4$. In some embodiments, the magnetic ferrite crystallizes in the spinel crystal structure. The spinel crystal structure is characterized by a cubic close packed lattice of anions (in this case oxygen anions), in which the cations (M and Fe) occupy some or all of the tetrahedral sites and octahedral sites. In the normal spinel structure, divalent cations occupy tetrahedral holes and trivalent cations occupy octahedral holes. In the inverse spinel structure, the divalent cations occupy octahedral holes while half of the trivalent cations occupy octahedral holes, and the other half of the trivalent cations occupy tetrahedral holes. Intermediate structures between these end members with different cation ordering schemes also exist, including random cation distribution (also known as cation disordered structures). In some embodiments, the magnetic ferrite crystallizes in the normal spinel structure. In alternative embodiments, the magnetic ferrite crystallizes in the inverse spinel structure. In other alternative embodiments, the magnetic ferrite crystallizes in an intermediate spinel structure.

In some embodiments, the magnetic ferrite is present in an amount of 15 to 45 wt %, preferably 17.5 to 42.5 wt %, preferably 20 to 40 wt %, preferably 22.5 to 37.5 wt %, preferably 25 to 35 wt %, preferably 27.5 to 32.5 wt %, preferably 29 to 31 wt %, preferably 30 wt %, based on a total weight of the nanocarrier.

In general, the magnetic ferrite particles can be any shape known to one of ordinary skill in the art as described above. In some embodiments, the magnetic ferrite has a mean particle size of 0.5 to 50 nm, preferably 0.75 to 25 nm, preferably 1 to 15 nm, preferably 1.5 to 10 nm.

The incorporation of the magnetic ferrite particles occupies a portion of the pores present in the porous silicate matrix. In some embodiments, the incorporation of the magnetic ferrite particles reduces a post-ferrite incorporation pore volume of the porous silicate matrix to 5 to 75%, preferably 7.5 to 70%, preferably 10 to 67.5%, preferably 12.5 to 65%, preferably 15 to 62.5% of an initial pore volume of the porous silicate matrix. That is, the nanocarrier has a pore volume of 5 to 75%, preferably 7.5 to 70%, preferably 10 to 67.5%, preferably 12.5 to 65%, preferably 15 to 62.5% of the pore volume of the porous silicate matrix. In some embodiments in which the porous silicate matrix is MCM-41, the nanocarrier has a total pore volume of 0.0385 to 1.35 cc/g, 0.05 to 1.25 cc/g, preferably 0.1 to 1.0 cc/g, preferably 0.15 to 0.90 cc/g, preferably 0.20 to 0.85 cc/g, preferably 0.25 to 0.80 cc/g, preferably 0.30 to 0.75 cc/g, preferably 0.35 to 0.70 cc/g, preferably 0.40 to 0.65 cc/g, preferably 0.45 to 0.60 cc/g, preferably 0.50 to 0.55 cc/g. In some embodiments in which the porous silicate matrix is mesosilicalite, the nanocarrier has a total pore volume of 0.03 to 0.45 cc/g, preferably 0.05 to 0.30 cc/g, preferably 0.075 to 0.20 cc/g, preferably 0.9 to 0.15 cc/g, preferably 0.1 cc/g.

In general, the anti-cancer therapeutic may be any suitable anti-cancer therapeutic known to one of ordinary skill in the art. Exemplary anti-cancer therapeutics include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, platinum-containing anti-cancer therapeutics, and mixtures thereof.

In preferred embodiments of the invention, the anti-cancer therapeutic comprises a platinum (II) complex. Any platinum(II) complexes effective for treatment of cancer can be used including, but not limited to, cisplatin, carboplatin, oxaliplatin, nedaplatin, triplatin tetranitrate, phenanthriplatin, picoplatin, strataplatin or mixtures thereof. In some embodiments, the platinum(II) complex is at least one selected from the group consisting of cisplatin, carboplatin, and oxaliplatin. In preferred embodiments, the platinum (II) complex is cisplatin.

In alternative preferred embodiments, the anti-cancer therapeutic comprises tamoxifen.

In general, the antioxidant may be any suitable antioxidant known to one of ordinary skill in the art. Examples of such antioxidants include, but are not limited to curcumin (and curcumin derivatives known as curcuminoids), Coenzyme Q10, quercetin, rutin, ascorbic acid, gallic acid, edaravone, N-acetylcysteine, alfa-lipoic acid, diosmin, hesperidin, oxerutins, baicalein, tocotrienols, resveratrol or other stilbenoids such as pterostilbene, retinoids and carotenes including Vitamin A, beta carotene, and alpha-carotene, astaxanthin, canthaxanthin, lutein, lycopene, and zeaxanthin, natural phenols including flavonoids, silymarin, xanthones, eugenol, phenolic acids, lipoic acid, acetylcysteine, uric acid, glutathione, and catechin. In some embodiments, the antioxidant is at least one selected from the group consisting of quercetin, rutin, coenzyme Q10, gallic acid, and curcumin.

Quercetin has the following chemical structure:

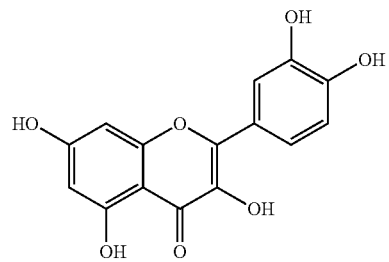 [SMILES: O=c1c(O)c(-c2ccc(O)c(O)c2)oc2cc(O)cc(O)c12]

Quercetin is a plant flavonol from the flavonoid group. It is found in a wide variety of food sources, but has very low water solubility and bioavailability. Inclusion of quercetin in the nanomedicinal composition of the present invention may overcome these disadvantageous properties of quercetin to increase an amount of quercetin which is delivered. Quercetin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-wt. %, 30-70 wt. %:70-30 wt. %, 40-60 wt. %:60-40 wt. % or about 50 wt. %:about 50 wt. % (or any intermediate ratio of crystalline:amorphous forms).

Rutin has the following structure:

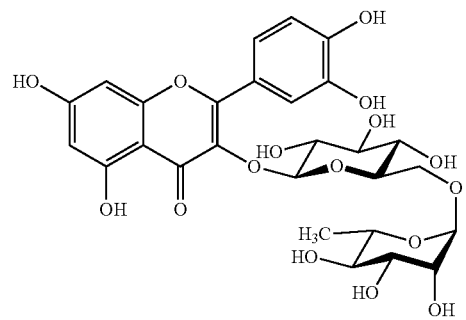

Rutin is the glycoside combining the flavonol quercetin and the disaccharide rutinose (α-L-rhamnopyranosyl-(1→6)-β-D-glucopyranose). Rutin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline: amorphous forms).

Coenzyme Q10 (CoQ10) conforms to the following chemical structure:

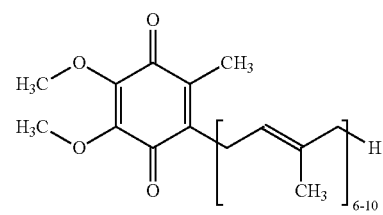

CoQ10 is a 1,4-benzoquinone, where Q refers to the quinone chemical group and 10 refers to the number of isoprenyl chemical subunits in its tail. Other forms of Coenzyme Q may be distinguished from CoQ10 by their number of isoprenyl subunits. A CoQ such as CoQ10 may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 20 wt. %, 40-60 wt. %:60-40 wt. % or about 50 wt. %:about 50 wt. % (or any intermediate ratio of crystalline: amorphous forms).

Gallic acid has the following structure:

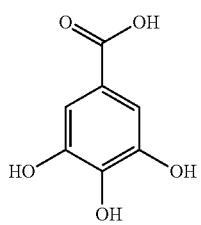

Gallic acid is a potent antioxidant against cancers (leukemia, colon and lung cancer cells) and other metabolic disorders. Gallic acid may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %: 60-40 wt. % or about 50 wt. %:about 50 wt. % (or any intermediate ratio of crystalline: amorphous forms).

Curcumin has the following structure:

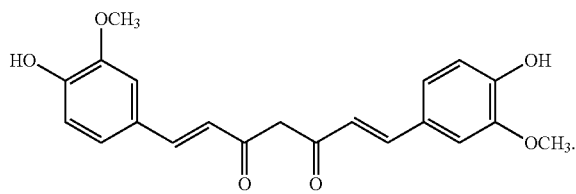 [SMILES: COc1cc(/C=C/C(=O)CC(=O)/C=C/c2ccc(O)c(OC)c2)ccc1O]

A curcuminoid is a linear diarylheptanoid. This class of compounds includes curcumin in both its keto and enolate forms as well as curcumin derivatives such as demethoxycurcumin and bisdemethoxycurcumin and their geometrical isomers and metabolites including sulfate conjugates and glucoronides. Other examples of curcumin derivatives or analogs include those 10 described by Raja, et al., U.S. Pat. No. 9,447,023 B2, Raja, et al., U.S. Pat. No. 9,650,404 B2, Johnson, et al., U.S. Pat. No. 9,556,105 B2 or Vander Jagt, et al., U.S. Pat. No. 9,187,397 B2 (all incorporated by reference); especially for their descriptions of curcuminoid formulas and various chemical species of curcuminoids. In some embodiments of the invention curcumin or another curcuminoid may be included as an antioxidant in the nanomedicinal composition of the present disclosure.

Mixtures of curcuminoids are also contemplated such as one isolated from rhizomes of turmeric comprised of Curcumin (75-81%), Demethoxycurcumin (15-19%) and Bisdemethoxycurcumin (2.5-6.5%). The content of any one of a curcuminoid in a mixture may range from about 0 to about 100 wt. %, for example, 10-90 wt. %, 20-80 wt. %, 30-70 wt. %, 40-60 wt %, 50 wt. %, 40 wt. %, 33.3 wt. %, 30 wt. %, 20 wt. %, 10 wt. % or 5 wt % or 1 wt. %. A mixture may contain two, three or more different curcuminoids.

Curcumin may be present in a crystalline or amorphous form or in a mixture of both crystalline and amorphous forms, for example at a ratio of 1-99 wt. %:99-1 wt. %, 10-90 wt. %: 90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline: amorphous forms). In some embodiments disclosed herein, curcumin will be in an amorphous form to increase its solubility.

Curcumin and its derivatives are known for their antimicrobial, anti-oxidative, anti-inflammatory, and anti-cancer properties such as malignancies in the brain or nervous system. Curcumin has also been proposed as an agent to treat oxidative stress, such as oxidative stress in the brain, and for treatment of neurodegenerative disease like Alzheimer's disease ("AD") or Parkinson's disease ("PD"); Lee, et al., Curr. Neuropharmacol. 2013 July; 11(4):338-378 (incorporated by reference).

Curcumin may also be functionalized or prepared as a conjugate with another moiety to modify or improve its pharmacokinetic properties. For example, curcumin can be adsorbed through functionalization to a silane, carboxylic acid, or biotin. Biocompatibility of a curcuminoid/hierarchical aluminosilicate can be increased by the modification with chitosan, or poly (D,L-lactide-co-glycolide), or polyethylene glycol.

In preferred embodiments, the antioxidant is curcumin.

In some embodiments, a weight ratio of the antioxidant to the anti-cancer therapeutic is 1:1 to 10:1, preferably 2:1 to 9:1, preferably 3:1 to 8:1, preferably 4:1 to 7:1, preferably 5:1 to 6:1.

In some embodiments, the pharmaceutical agent mixture is present in the nanomedicinal composition in an amount of 5 to 50 wt %, preferably 10 to 47.5 wt %, preferably 15 to 45 wt %, preferably 17.5 to 42.5 wt %, preferably 20 to 40 wt %, preferably 22.5 to 37.5 wt %, preferably 25 to 35 wt %, preferably 26 to 34 wt %, preferably 27 to 33 wt %, preferably 28 to 31 wt %, preferably 29 to 30 wt %, based on a total weight of nanomedicinal composition.

In some embodiments, the nanomedicinal composition comprises a biocompatible coating. Such a biocompatible coating may be disposed upon the nanocarrier and/or the pharmaceutical agent mixture. In general, the biocompatible coating may be any suitable coating known to one of ordinary skill in the art. Examples of such suitable biocompatible coatings include, but are not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly (DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate.

In some embodiments, the nanomedicinal composition releases greater than 10 wt %, preferably greater than 12.5 wt %, preferably greater than 15 wt %, preferably greater than 17.5 wt %, preferably greater than 20 wt %, preferably greater than 22.5 wt %, preferably greater than 25 wt %, preferably greater than 27.5 wt %, preferably greater than 30 wt %, preferably greater than 32.5 wt %, preferably greater than 35 wt %, preferably greater than 37.5 wt %, preferably greater than 40 wt % of a total weight of the antioxidant. In some embodiments, this release occurs within 20 hours, preferably within 18 hours, preferably within 16 hours, preferably within 14 hours, preferably within 12 hours of contact with a suitable biological medium. Examples of suitable biological media include, but are not limited to, buffered saline solutions such as phosphate buffered saline, cell culture media such as Minimum Essential Medium (MEM, also known as Eagle's minimal essential medium EMEM), Dulbecco's Modified Eagle's Medium (DMEM), Iscove's Modified Dulbecco's Medium (IMDM), RPMI-1640, Ham's F-10, and F-12; animal tissue, or a subject's body. In some embodiments, the nanomedicinal composition releases greater than 50 wt %, preferably greater than 52.5 wt %, preferably greater than 55 wt %, preferably greater than 57.5 wt %, preferably greater than 60 wt %, preferably greater than 62.5 wt %, preferably greater than 65 wt %, preferably greater than 67.5 wt %, preferably greater than 70 wt %, preferably greater than 72.5 wt %, preferably greater than 75 wt %, preferably greater than 77.5 wt %, preferably greater than 80 wt % of a total weight of the anti-cancer therapeutic.

In a preferred aspect of the invention the antioxidant is provided as an outer component of the nanomedicinal composition. As an outer component the antioxidant is mainly located or disposed at an outside surface of particles of the nanomedicinal composition. The position of the antioxidant mainly at the surface or enriched at the surface can be achieved by treating a composition that contains the porous silicate, the magnetic ferrite and the anti-cancer therapeutic with antioxidant particles or, preferably, a solution comprising an antioxidant agent. Subsequent drying of the resultant particles preferentially disposes the antioxidant at an exterior portion of particles of the nanomedicinal composition. In other embodiments the antioxidant is present throughout the nanomedicinal composition and, in addition, is a main component of the exterior surface of the nanomedicinal composition. This structure of the nanomedicinal composition is obtained by preparing a nanomedicine medicinal composition containing the porous silicate, magnetic ferrite, anti-cancer therapeutic, and antioxidant in particulate form then treating the resulting particulate material with a solution of the same antioxidant or a second antioxidant to place the antioxidants at an exterior and/or surface location of the nanomedicinal composition.

Placing the antioxidant at a surface position of particles of the nanomedicinal composition provides an important benefit. One aspect that may be positively affected is the release rate of the pharmaceutical agent mixture. The antioxidant may inhibit release of the pharmaceutical agent mixture for a time period while the nanomedicinal composition travels through the vascular system of a patient undergoing treatment. This provides an induction period during which only minor amounts of the pharmaceutical agent mixture are released. When the pharmaceutical agent mixture reaches a target site, such as a tumor, for example by application of a magnetic field to direct the particles to the tumor, the induction period has delayed release of the pharmaceutical agent mixture. Upon arrival at the target site the nanomedicinal composition may be held in place (for example by application of a strong magnetic field) and release the pharmaceutical agent mainly at the target site. The release of the pharmaceutical agent mixture may be facilitated by an acidic pH at a tumor site. Such facilitation may, for example, take the form of an increased rate of release, an increased total amount released, or both.

In this aspect of the invention the release of the pharmaceutical agent may be due over a release period of at least 2 hours, preferably at least 4 hours, preferably at least 6 hours, preferably at least 8 hours, preferably at least 10 hours, preferably at least 12 hours, preferably at least 14 hours, preferably at least 16 hours, preferably at least 18 hours, preferably at least 20 hours Initial release rates are preferably 10 wt % of the total amount of pharmaceutical agent in the nanomedicinal composition during the induction period. Upon passage of the induction period and arrival of the nanomedicinal composition at a target site, a major portion of the pharmaceutical agent is released. In some embodiments, the major portion comprises at least 25 wt %, preferably at least 30 wt %, preferably at least 35 wt %, preferably at least 40 wt %, preferably at least 45 wt %, preferably at least 50 wt % of a total amount of pharmaceutical agent released.

In some embodiments, the induction period is provided by a coating disposed on the nanomedicinal composition, the coating as described above. In such embodiments, the coating may inhibit the release of the pharmaceutical agent mixture. Removal of the coating by any suitable process, for example by dissolving, degrading, or digesting, may allow the pharmaceutical gent mixture to be released.

In some embodiments, the nanomedicinal composition has an antioxidant release rate of 0.1 to 10 wt % per hour, preferably 0.25 to 9 wt % per hour, preferably 0.5 to 7.5 wt % per hour, preferably 0.75 to 5 wt % per hour, preferably 1 to 4 wt % per hour based on a total initial weight of antioxidant. In such embodiments, the antioxidant release rate may be an average antioxidant release rate measured over the release period as described above. In some embodiments, the nanomedicinal composition has an initial antioxidant release rate which is maintained over an initial release period. In such embodiments, the initial release period may be followed by a second release period which has a second antioxidant release rate. The initial antioxidant release rate and/or second antioxidant release rate may be average release rates as described above. In some embodiments, the nanomedicinal composition has an anti-cancer therapeutic release rate of 0.5 to 15 wt % per hour, preferably 1 to 14 wt % per hour, preferably 2.5 to 13 wt % per hour, preferably 5 to 11 wt % per hour, preferably 6 to 10 wt % per hour based on a total initial weight of anti-cancer therapeutic. In such embodiments, the anti-cancer therapeutic release rate may be an average anti-cancer therapeutic release rate measured over the release period as described above. In some embodiments, the nanomedicinal composition has an initial anti-cancer therapeutic release rate which is maintained over an initial release period. In such embodiments, the initial release period may be followed by a second release period which has a second anti-cancer therapeutic release rate. The initial anti-cancer therapeutic release rate and/or second anti-cancer therapeutic release rate may be average release rates as described above. In some embodiments, the initial release period comprises the first 20 hours of release, preferably the first 18 hours of release, preferably the first 16 hours of release, preferably the first 14 hours of release, preferably the first 12 hours of release, preferably the first 10 hours of release. Such "first hours of release" are preferably measured from the initiation of release. The initiation of release may be measured by, for example a delivery of the nanomedicinal composition to a tumor site, the application of a magnet or magnetic field to target the nanomedicinal composition to a tumor site, the application of an alternating magnetic field for magnetic heating, or a pre-determined amount of time after administration. Such a pre-determined time may be any suitable amount of time known to one of ordinary skill in the art, for example, an expected time for delivery of the nanomedicinal composition to the tumor site, an expected circulation time, an expected coating degradation time, or the like.

The present disclosure also relates to a method of forming the nanomedicinal composition, the method comprising mixing an M(II) salt and a Fe(III) salt with the porous silicate matrix to form a powdery mixture, calcining the powdery mixture to form the nanocarrier, mixing the nanocarrier and the anti-cancer therapeutic in an aqueous solution thereby forming a therapeutic-containing nanocarrier, and mixing the therapeutic-containing nanocarrier and the antioxidant in an impregnation solution thereby forming the nanomedicinal composition.

In general, any suitable M(II) salt known to one of ordinary skill in the art may be used. Examples of such suitable M(II) salts include, but are not limited to halide salts, acetate salts, oxalate salts, formate salts, hydroxide salts, sulfate salts, sulfite salts, phosphate salts, hydrogen phosphate salts, dihydrogen phosphate salts, carbonate salts, bicarbonate salts, and nitrate salts. Preferably, the M(II) salt does not comprise an anion which itself comprises a metal, such as chromate salts, aluminate salts, and arsenate salts. In preferred embodiments, the M(II) salt is a nitrate salt. The M(II) salt may be used in anhydrous form or in hydrate form.

In general, any suitable Fe(III) salt known to one of ordinary skill in the art may be used, as described above. In preferred embodiments, the Fe(III) salt is Fe(III) nitrate. The Fe(III) salt may be used in anhydrous form or in hydrate form.

In some embodiments, the calcining is performed at a temperature of 700 to 1,000° C., preferably 725 to 975° C., preferably 750 to 950° C., preferably 775 to 925° C., preferably 800 to 900° C., preferably 825 to 875° C., preferably 840 to 860° C., preferably 850° C. The calcining step may be carried out under air, nitrogen, argon or a combination thereof. The mixture of gas may be 60% to 100%, or 70% to 90% nitrogen and 0% to 80%, 10% to 70%, or 30% to 50% argon. In preferred embodiments, the calcining is performed in ambient air. In some embodiments, the calcining is performed for 1 to 12 hours, preferably 1.5 to 11 hours, preferably 2 to 10 hours, preferably 2.5 to 9.5 hours, preferably 3 to 9 hours, preferably 3.5 to 8.5 hours, preferably 4 to 8 hours, preferably 4.5 to 7.5 hours, preferably 5 to 7 hours, preferably 5.5 to 6.5 hours, preferably 6 hours.

In some embodiments, the aqueous solution is a saline. In preferred embodiments, the aqueous solution is phosphate buffered saline. In some embodiments, the anti-cancer therapeutic is present in the aqueous solution at a concentration of 1.0 to 20.0 mM. preferably 2.5 to 17.5 mM, preferably 5.0 to 15.0 mM, preferably 7.5 to 12.5 mM, preferably 8.0 to 11.0 mM, preferably 9 to 11.0 mM, preferably 9.5 to 10.5 mM, preferably 10.0 mM. In some embodiments, the nanocarrier is present in the aqueous solution at a concentration of 20 to 100 mg/mL, preferably 30 to 90 mg/mL, preferably 35 to 85 mg/mL, preferably 40 to 80 mg/mL, preferably 45 to 75 mg/mL, preferably 50 to 70 mg/mL, preferably 55 to 65 mg/mL, preferably 60 mg/mL.

In some embodiments, the impregnation solution comprises an alcohol solvent. In some embodiments, the alcohol solvent is methanol. In some embodiments, the impregnation solution comprises water. In some embodiments, the impregnation solution comprises glycerol. In some embodiments, the antioxidant is present in the impregnation solution at a concentration of 1.0 to 20.0 mM, preferably 2.5 to 17.5 mM, preferably 5.0 to 15.0 mM, preferably 7.5 to 12.5 mM, preferably 8.0 to 11.0 mM, preferably 9 to 11.0 mM, preferably 9.5 to 10.5 mM, preferably 10.0 mM. In some embodiments, the therapeutic-containing nanocarrier is present in the impregnation solution at a concentration of 2 to 30 mg/mL, preferably 4 to 28 mg/mL, preferably 6 to 26 mg/mL preferably 8 to 24 mg/mL, preferably 10 to 22 mg/mL, preferably 12 to 20 mg/mL, preferably 13 to 19 mg/mL, preferably 14 to 18 mg/mL, preferably 15 to 17 mg/mL, preferably 16 mg/mL.

The present disclosure also relates to a method for treating a cancer in a subject, the method comprising administering to a subject in need of therapy a pharmaceutical composition comprising the nanomedicinal composition. The cancer is at least one selected from the group consisting of breast cancer, colorectal cancer, and lung cancer. In preferred embodiments, the cancer is breast cancer. The pharmaceutical composition may further comprise one or more pharmaceutically acceptable carriers.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a pharmaceutical composition will depend upon the intended route of administration for the pharmaceutical composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl—ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as gels, pastes, and suppositories, liquid dosage forms such as suspension, and dispersions, inhalation dosage form such as aerosols, sprays, and powders.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection dispersions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These dispersions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal cancer, but may be unsuitable for treating other cancers.

Administration by inhalation may be advantageous for treating lung cancer, but may be unsuitable for treating other cancers.

In other embodiments, the pharmaceutical composition comprising the nanomedicinal composition disclosed herein thereof has different release rates categorized as immediate release and controlled- or sustained-release.

The presence of the particles of a magnetic ferrite in the nanomedicinal composition may serve one or more purposes. A first purpose may be to aid targeting the drug to a particular diseased tissue by applying external magnetic field to the diseased tissues, and thereby concentrating the drug in the diseased tissues in need of treatment and minimize the drug contacts with healthy tissues. A second purpose may be that the particles of a magnetic ferrite are magnetic contrasting agent used in magnetic resonance (MM) imaging. Thus, the method of treatment may involve a combination of administering effective amount of the drug to a subject, while observing and targeting the drug to the diseased tissue by an applied external magnetic field. A third purpose may be that the particles of a magnetic ferrite may be used in magnetic heating. Such heating is a response to exposure of the nanocarrier to an alternating magnetic field. Such heating may be useful for a purpose such as increasing the rate of anti-cancer therapeutic and/or antioxidant release, increasing the amount of anti-cancer therapeutic and/or antioxidant released, and/or hyperthermia treatment of cancer. Hyperthermia treatment is a treatment method which involves heating a tissue, tumor, or other area to a temperature above its normal temperature. Such heating may be achieved by the application of an alternating magnetic field to a magnetic material co-located with the desired treatment area, laser heating, microwave heating, or any other suitable heating method known to one of ordinary skill in the art. In some embodiments, the method further comprises exposing the subject to an alternating magnetic field, thereby raising the temperature of the nanomedicinal composition.

As used herein, the terms "treat", "treatment", and "treating" in the context of the administration of a therapy to a subject in need thereof refers to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the pharmaceutical compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and rectal administration. Those of ordinary skill in the art are familiar with administration techniques that can be employed with the compounds and methods described herein. In preferred embodiments, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the nanomedicinal composition per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering the pharmaceutical composition of the current disclosure as a single dose or multiple individual divided doses and applying a magnetic field to the diseased tissue, wherein the nanomedicinal composition is accumulated and releases the loaded anti-cancer therapeutic and/or antioxidant in or nearby the diseased tissues. In some embodiments, the pharmaceutical composition is administered at various dosages (e.g. a first dose with an effective amount of nanomedicinal composition comprising 200 mg of the anti-cancer therapeutic per kilogram of the subject and a second dose with an effective amount of the nanomedicinal composition comprising 50 mg of the anti-cancer therapeutic per kilogram of the subject). In some embodiments, the interval of time between the administration of the pharmaceutical composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical composition is administered once daily for at least 2 days, 5 days, 6 days, or 7 days. In certain embodiments, the pharmaceutical composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments of treatment, the method further comprises measuring a concentration of a biomarker and/or detecting a mutation in a biomarker before and/or after the pharmaceutical composition comprising the nanomedicinal composition of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by any suitable procedure known to one of ordinary skill in the art, such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the nanomedicinal composition by at least 5%, at least 10%, or at least 30%, up to 50%, up to 60%, or up to 80% of an initial effective amount nanomedicinal composition that contains in the range of 1-300 mg of the anti-cancer therapeutic per kilogram of the body weight of the subject. The increased effective amount may be in a range of 1.05-540 mg/kg, preferably 15-420 mg/kg, more preferably 25-270 mg/kg.

The subject may be administered with the increased dosage for a longer period (e.g. one more week, 2 more weeks, or 2 more months) than the duration prescribed with the initial effective amount.

In some embodiments, the mutation in the biomarker is detected before administering the pharmaceutical composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, weeks, 40-50 weeks, 1 year, 2 years, or any period of time in between after the administration.

In some embodiments, the administration is stopped once the subject is treated.

The examples below are intended to further illustrate protocols for preparing, characterizing, and using the nanomedicinal composition or for treating a cancer using the nanomedicinal composition and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

Examples

Ludox AS-40 (silica source), Tetrapropylammonium bromide (micropore template), Cetyltrimethyl ammonium bromide (mesoporous template), $Cu(NO_3)_2 \cdot 3H_2O$, $Fe(NO_3)_3 \cdot 9H_2O$, and cisplatin were purchased from Sigma Aldrich. Curcumin was obtained from Molecule on (New Zealand). Q-10 silica with pore diameter of about 18 nm was obtained from Fuji Silysia Chemical Ltd. Spherical hydrophobic silica was purchased from Superior Silica, USA. All the reagents used in in vitro study were of analytical grade. Gibco cell culture products such as DMEM (Dulbecco's Modified Eagle Medium), heat-inactivated fetal bovine serum (HI-FBS), 100× Penicillin Streptomycin, and 100× MEM NEAA (MEM non-essential amino acids) were obtained from Thermo Fisher. 3-(4,5-dimethylthiazol-2-yl)-2,5-diphenyltetrazolium bromide (MTT) reagent, cat. M2128 was purchased from Sigma-Aldrich. Hoechst 33342 nuclear stain, cat. 62249, and cleaved-Caspase antibody 3 (c-Caspase 3), cat. 9661, were procured from Thermo Scientific and Cell Signaling, respectively. Alexa Fluor 594 goat anti-rabbit secondary antibody, cat. R37117 was obtained from Invitrogen.

Preparation of 30% $CuFe_2O_4$/Mesosilicalite and 30% CuFe2O4/MCM-41

Mesosilicalite was prepared by disintegrating silicalite crystals in alkaline medium following the top-down approach. A detailed synthesis procedure for mesosilicalite, MCM-41, SBA-16, and mesobeta are provided in Vijaya Ravinayagam; Rabindran Jermy, B., J. Nanopart Res. 2017, 19, 190, incorporated herein by reference in its entirety. The copper ferrite impregnated mesosilicalite and MCM-41 was prepared by dry mixing. Briefly, 0.61 g of copper nitrate trihydrate, 1.01 g of iron nitrate nonahydrate and 1.4 g of predried structured silica was physically mixed for 30 min using mortar pistol. The obtained mixture was calcined at 850° C. for 6 h.

Curcumin coating and Cisplatin functionalization over 30% $CuFe_2O_4$/Mesosilicalite and 30% CuFe2O4/MCM-41

40 mg of curcumin was dissolved in 10 ml of methanol for 10 min. Then 160 mg of cisplatin loaded mesosilicalite or MCM-41 was added and the mixture was sonicated for 2 min. Then the solvent was evaporated using rotary evaporator.

Cisplatin (30 mg) was first added in normal saline solution (10 ml) and stirred to form a clear solution. Then, copper ferrite nanocomposite (600 mg) was added and stirred overnight under ice cold dark environment. The solution was then filtered, washed and dried. The functionalized cisplatin was calculated using UV-visible spectroscopy at 208 nm.

Characterization Techniques

The phase of support carriers $CuFe_2O_4$/mesosilicalite, $CuFe_2O_4$/MCM-41, $CuFe_2O_4$/SBA-16, $CuFe_2O_4$/Hydrophobic silica, $CuFe_2O_4$/MesoZ SM-5 and $CuFe_2O_4$/Mesobeta was identified using benchtop XRD (Miniflex 600, Rigaku, Japan). The textural features including BET surface area, pore size and pore volume were measured using nitrogen adsorption technique (ASAP-2020 plus, Micromeritics, USA). The ferrite nanoparticle chemical coordination was analyzed using DRS-UV-visible spectroscopy analysis (JASCO, Japan). Vibrating sample magnetometer (LDJ electronics, 9600) was used to determine the magnetic property of $CuFe_2O_4$/mesosilicalite and $CuFe_2O_4$/MCM-41. The functional groups of curcumin, cisplatin in nanoformulation were determined using FT-IR spectroscopy (Perkin Elmer). The morphological variations of spinel ferrite/mesosilicalite/curcumin/cisplatin were investigated using transmission electron microscopy (TEM, JEM2100F, JEOL).

Drug Release Study

The release trend of curcumin and cisplatin was investigated using different nanoformulations. Curcumin release was carried out by dissolving 30 mg of curcumin loaded sample in 50 ml of PBS (pH 5.6). 10 ml of solution was withdrawn and replaced with equal volume of fresh solution. The release content was identified at specific wavelength of 428 nm.

Prior to the cisplatin release study, the dialysis membrane was activated and then 30 mg of nanoformulation was dispersed in 50 ml of PBS solution (pH 5.6). The cisplatin release was monitored at 37° C. At regular time intervals, 10 ml of solution was withdrawn and cisplatin release was measured using UV-visible spectroscopy. The withdrawn solution was replaced with equal volume of fresh PBS solution.

Cell Lines and Cell Culture Setting

Human mammary adenocarcinoma (MCF7) and the non-cancerous human foreskin fibroblasts (HFF) cell lines were used to assess the cytotoxic effect of the prepared compounds. Cells were cultured in a DMEM culture medium containing 10% HI-FBS, 1% Penicillin Streptomycin, and 1% MEM NEAA. Cells were maintained in a humidified setting at 37° C. with 5% $CO_2$. For cell viability assay, cells were seeded in a 96-well plate with a density of 20,000 cells/well. While for microscopic images, 50,000 cells/well were plated on an eight-well chamber slide. On the following day, cells were switched to the starve culture medium that contains 0.5% HI-FBS. Cells were maintained for 24 h in the starve medium before the treatment was added.

Cell Treatment

MCF7 and HFF cells were treated with the subsequent conditions for 48 h: $CuFe_2O_4$/Mesosilicalite, Curcumin, Cisplatin, $CuFe_2O_4$/Mesosilicalite/Curcumin, $CuFe_2O_4$/Mesosilicalite/Curcumin/Cisplatin, or $CuFe_2O_4$/MCM-41/Curcumin/Cisplatin. Treatment concentrations of $CuFe_2O_4$/Mesosilicalite, $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin nanocomposites were: 0.025, 0.05, 0.1, and 0.5 mg/ml. Based on the drug loading experiments, simple calculations were followed to reflect the actual quantity of curcumin and cisplatin that adsorbed on $CuFe_2O_4$/Mesosilicalite nanoparticles. According to the loading experiments, 1 mg of $CuFe_2O_4$ nanoparticles contains 0.25 mg and 0.045 mg of curcumin and cisplatin, respectively. Thus, if $CuFe_2O_4$/Mesosilicalite concentration was 0.5 mg/ml, there is 0.125 mg/ml of adsorbed curcumin and 0.0225 mg/ml of functionalized cisplatin. Therefore, the treatment concentrations of curcumin were: 0.00625, 0.0125, 0.025 and 0.125 mg/ml and the treatment concentrations of cisplatin were: 0.001125, 0.00225, 0.0045 and 0.0225 mg/ml.

Cell Viability (MTT) and EC50

To assess the compounds' cytotoxicity, 3-(4,5-dimethylthiazol-2-yl)-2,5-diphenyltetrazolium bromide (MTT), a cell viability assay, was used. It measures the cell viability by assessing the mitochondria's ability to convert yellow MTT solution into purple formazan insoluble crystals. Following Mosmann's protocol, 5 mg/ml of MTT powder was dissolved in PBS, and 0.5 mg/ml of MTT working solution was prepared [Mosmann, T., J Immunol Methods, 1983, 65, 55-6317]. Cells were washed with PBS and followed by the addition of 100 ul MTT working solution. All the experimental conditions were run in triplicates (technical repeats) with four biological repeats (n=4). The 96-well plate was incubated for three h at 37° C. An MTT negative control (background control) was included in the experimental setting by adding MTT working solution to wells that contain no cells. After the incubation time, 0.04 N HCl isopropyl alcohol was added to solubilize the formed formazan granules. The difference in color intensity was measured by SYNERGY-neo2 BioTek ELISA reader at 570 nm as a measuring wavelength. The technical triplicate readings of each condition were averaged, and the absorbance from MTT negative control was deducted from these readings. An initial reading was measured before MTT addition at the same wavelength. Thus, to remove undesirable interference in the measurement, the initial reading was subtracted from the final reading. Then, the treatment groups were analyzed by comparing them to the control (untreated cells). Cell viability was calculated using the following equation (1):

$$\% \text{ Cell Viability} = \frac{\text{averaged sample read}}{\text{averaged control read}} \times 100 \quad (1)$$

The cell viability assay data of the five biological repeats (n=5) were plotted on a graph against their corresponding dose. Afterward, the plotted data were used to extrapolate a best-fit line equation for each compound for MCF7 and HFF cell lines. These equations were used to calculate the half-maximal effective concentration (EC50) of each drug.

Immunofluorescent Staining and Microscopic Examination

Cells were plated in an 8-well chamber slide at a concentration of 50,000 cells/well. Cells were then treated for 48 h with the following conditions: $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin at a concentration of 0.5 mg/ml. Cells were fixed and stained with the apoptotic marker cleaved Caspase 3 (c-Caspase 3) antibody (1:200, Cell Signaling Technology) and incubated at 4° C. overnight. After PBS washing, Alexa Fluor 594-conjugated secondary antibody (Invitrogen, Thermo Fisher Scientific) was added to the cells at a final concentration of 1:1000 for 1 h at room temperature. Cells were then washed and stained with the nuclear stain Hoechst 33342 (Thermo Fisher Scientific) at a concentration of 2 µg/ml and incubated at room temperature for min. After staining, immunofluorescent images were taken using a confocal fluorescent microscope-Zeiss LSM 700. Bright-field images were captured using an inverted microscope-Nikon Eclipse TS100. Although both light and fluorescent pictures were taken from the same sample, they were not taken from the same field of view.

Statistics

The cell viability assay was performed in five independent experiments (n=5). Statistical analysis was performed using Prism 9 software (GraphPad, La Jolla, CA). The analysis was performed using one-way ANOVA with Dunnett's post hoc test. Error bars±S.E.M. *p<0.05; p<0.01; *p<0.001; ****p<0.0001 versus control. In case there was no indication of significance, it means that results were non-significant. The data analysis of drug delivery was done using Prism 8 software and SPSS software version 20.0.

Results

Figure 1B:
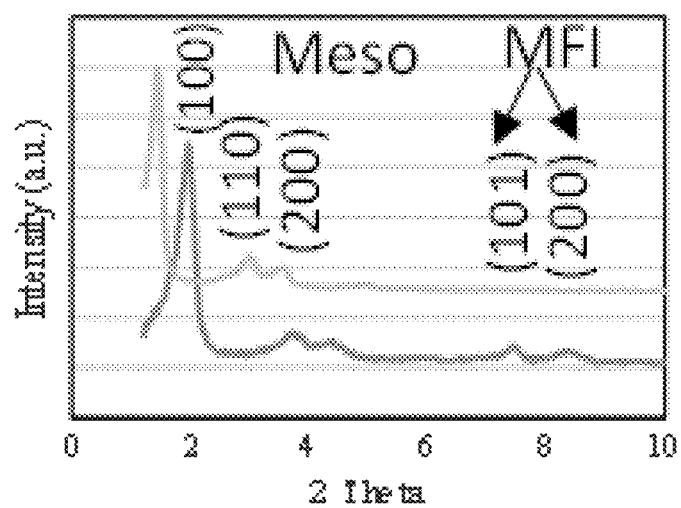
FIG. 1B shows a low-angle X-ray diffraction patterns of MCM-41 and Mesosilicalite showing the peaks corresponding to the peaks in common (Meso) and the peaks present in Mesosilicalite from the MFI structure type.
Figure 1C:
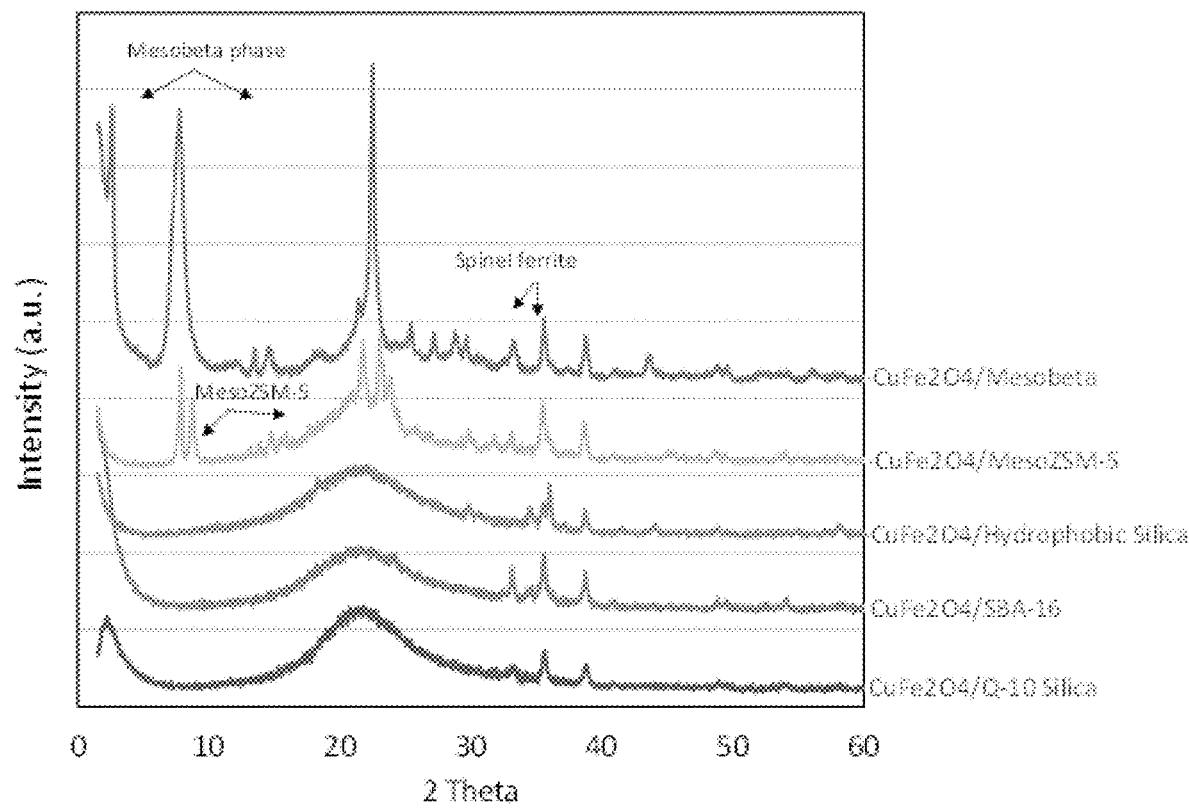
FIG. 1C shows X-ray diffraction pattern of $CuFe_2O_4$ impregnated on different structured mesoporous materials including Q-10 silica, SBA-16, hydrophobic silica, MesoZSM-5, and Mesobeta.

The X-ray diffraction pattern of meso and microphase of two supports were identified at low and high angle of MCM-41 and Mesosilicalite (FIG. 1A). The XRD pattern of $CuFe_2O_4$ impregnated over different structured nanocarriers are shown in FIGS. 1A-1C. Conventional MCM-41 showed a typical hexagonal structure with peaks at low angle corresponding to the plane (100), (110) and (200). Mesosilicalite showed the presence of MCM-41 and high silica zeolite peaks at 2 theta value of 7.9° and 8.7° corresponding to plane (101) and (200), respectively (See FIG. 1B). In the higher angle (20-60°), a broad peak of MCM-41 indicates the presence of amorphous framework bound to hexagonal phase. Mesosilicalite showed the typical characteristics peaks of MFI structure with corresponding to (321), (113), (501), (422) and (313) plane. In case of spinel impregnated MCM-41 and mesosilicalite, the presence of cubic phase of copper spinel appears with intense peak at 35.6° corresponding to (103) plane. A trace of a-$Fe_2O_3$ appears along with a less intense peak corresponding to CuO at 38.7° (See FIG. 1A).

Figure 2A:
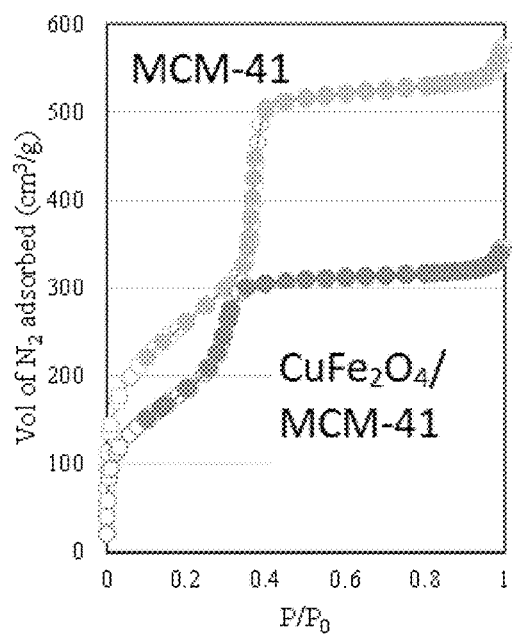
FIG. 2A is a plot of the nitrogen adsorption isotherm pattern of MCM-41 and $CuFe_2O_4$/MCM-41.
Figure 2B:
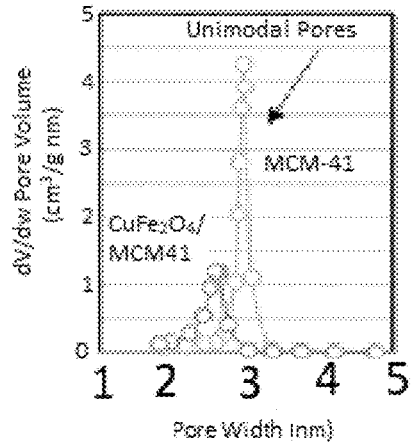
FIG. 2B is a plot of the pore size distribution for MCM-41 and $CuFe_2O_4$/MCM-41.
Figure 2C:
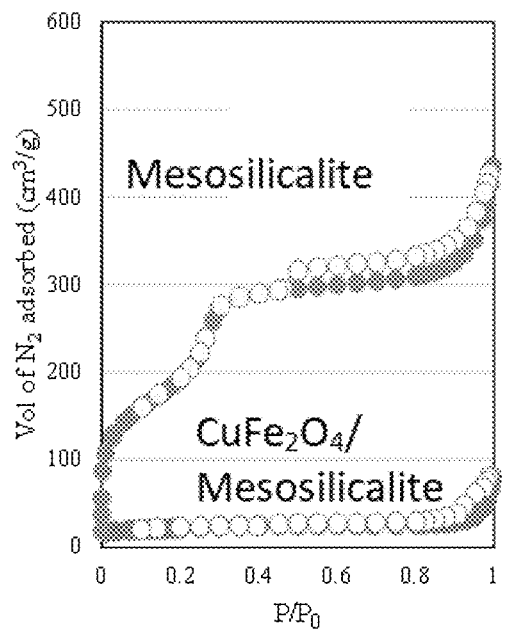
FIG. 2C is a plot of the nitrogen adsorption isotherm pattern of Mesosilicalite and $CuFe_2O_4$/Mesosilicalite.
Figure 2D:
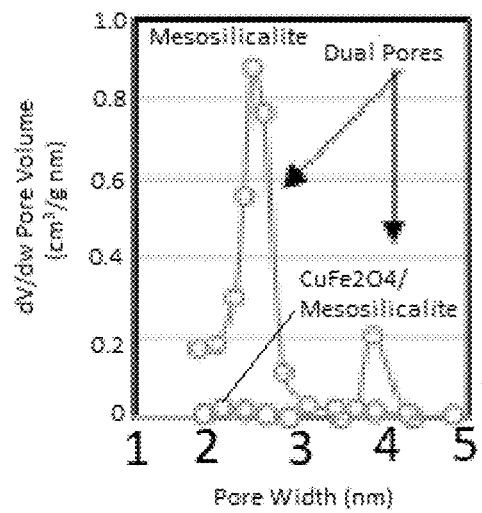
FIG. 2D is a plot of the pore size distribution for Mesosilicalite and $CuFe_2O_4$/Mesosilicalite.
Figure 2E:
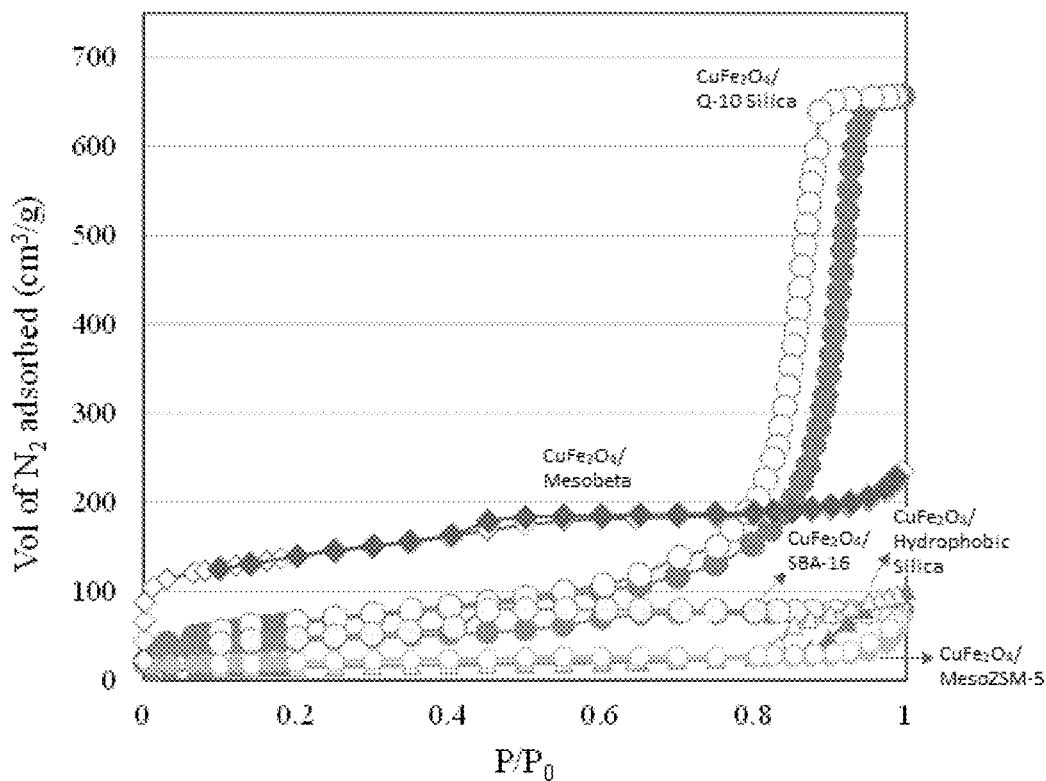
FIG. 2E is a plot of the nitrogen adsorption isotherm pattern of $CuFe_2O_4$ impregnated on different structured mesoporous materials including Q-10 silica, SBA-16, hydrophobic silica, MesoZSM-5, and Mesobeta.
Figure 2F:
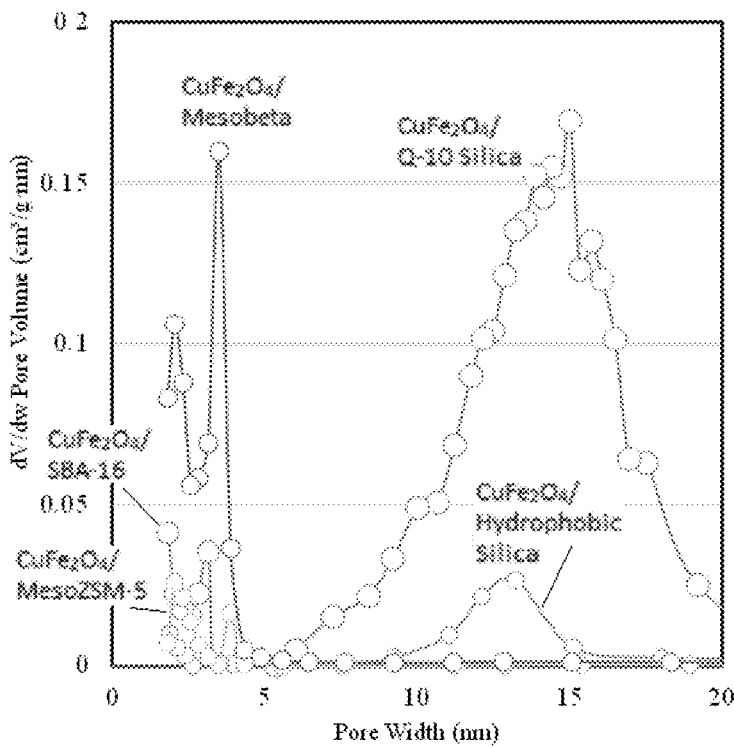
FIG. 2F is a plot of the pore size distribution for $CuFe_2O_4$ impregnated on different structured mesoporous materials including Q-10 silica, SBA-16, hydrophobic silica, MesoZSM-5, and Mesobeta.

The characteristics of textural surface, pore volume and average pore size of MCM-41, $CuFe_2O_4$/MCM-41, Mesosilicalite, and $CuFe_2O_4$/Mesosilicalite are shown in FIGS. 2A-2D. The surface area and pore size distribution of $CuFe_2O_4$ impregnated over different structured materials are shown in FIG. 2E and FIG. 2F, respectively. Before, spinel ferrite impregnation, MCM-41 showed a typical type IV isotherm indicating the presence of uniform pore size distributions (3.7 nm) with high surface area of 914 $m^2$/g and pore volume of 0.85 cc/g. In case of pure hexagonal mesopores of MCM-41, surprisingly, impregnation of spinel, only slightly reduced the surface area to 885 $m^2$/g, while pore volume reduced to 0.52 cc/g. In case of mesosilicalite, which contains micro and mesopores, the initial surface area of 804 $m^2$/g reduced significantly after impregnation to 74 $m^2$/g. An increase in dual pore sizes from 3.0 nm to 5.9 nm indicates the pore filling effect and formation of external pores in the hierarchical micro and mesopores after spinel ferrite loading. Pore volume reduction from 0.6 cc/g to 0.1 cc/g reflects the pore filling effect. Overall, the result shows unique deposition of spinel occurs over two supports. The textural characteristics vary depending on the structure of different shaped materials. A summary of these characteristics is presented in Table 1.

TABLE 1

Textural characteristics of 30% $CuFe_2O_4$ impregnated on different mesostructured materials

| Sample | BET Surface area (m²/g) | BJH adsorption cumulative surface area (m²/g) | Pore volume (cm³/g) | Average Pore Diameter (nm) |
|---|---|---|---|---|
| Mesosilicalite | 804 | 785 | 0.60 | 3.0 |
| $CuFe_2O_4$/Mesosilicalite | 70 | 31 | 0.10 | 5.9 |
| MCM-41 | 914 | 1116 | 0.85 | 3.7 |
| $CuFe_2O_4$/MCM-41 | 885 | 857 | 0.52 | 2.4 |
| SBA-16 | 988 | 591 | 0.69 | 2.79 |
| $CuFe_2O_4$/SBA-16 | 144 | 103 | 0.12 | 3.4 |
| Q-10 silica | 248 | 264 | 1.25 | 20.1 |
| $CuFe_2O_4$/Q-10 silica | 223 | 246 | 1.01 | 18.2 |
| Hydrophobic silica | 84 | 53 | 0.19 | 9.29 |
| $CuFe_2O_4$/Hydrophobic silica | 49 | 37 | 0.14 | 12.1 |
| Mesobeta | 533 (208)$^a$ | 341 | 0.39 | 2.9 |
| $CuFe_2O_4$/Mesobeta | 462 (157)$^a$ | 247 | 0.35 | 3.03 |
| MesoZSM-5 | 710 | 719 | 0.58 | 3.28 |
| $CuFe_2O_4$/MesoZSM-5 | 67 | 30 | 0.09 | 5.48 |

*$^a$micropore surface area

Figure 3:
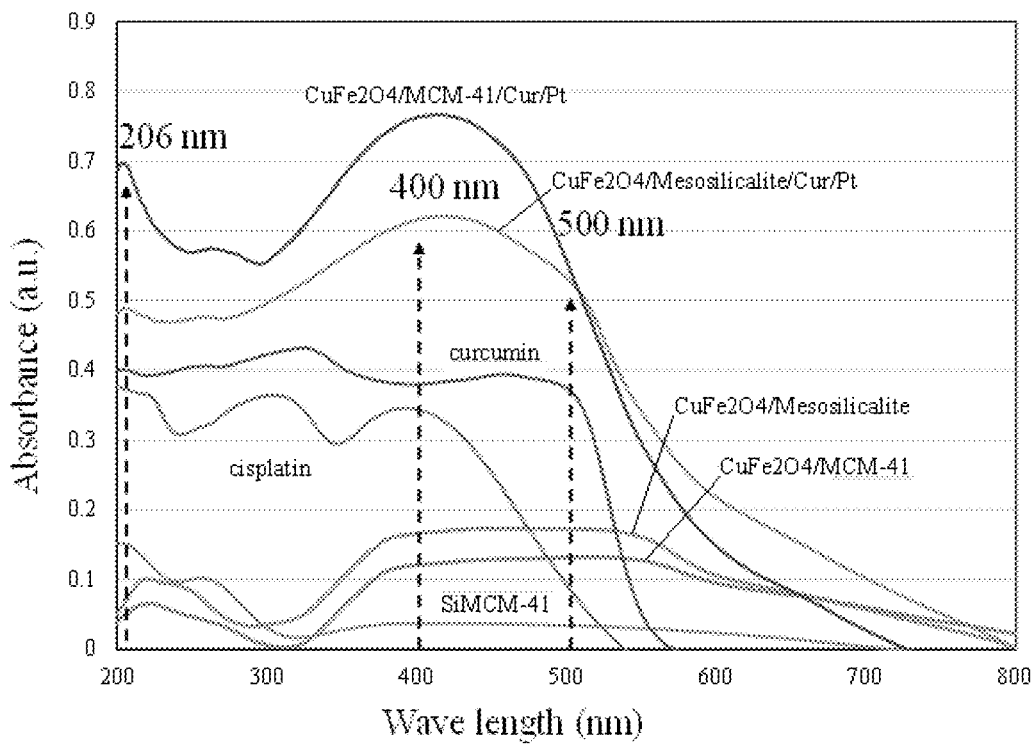
FIG. 3 shows diffuse reflectance UV-visible spectra of $CuFe_2O_4$/MCM-41 and $CuFe_2O_4$/Mesosilicalite.

FIG. 3 shows the diffuse reflectance UV-visible spectra of curcumin, cisplatin, MCM-41, $CuFe_2O_4$/MCM-41, $CuFe_2O_4$/mesosilicalite, $CuFe_2O_4$/MCM-41/curcumin/cisplatin and $CuFe_2O_4$/mesosilicalite/curcumin/cisplatin. Curcumin and cisplatin revealed broad absorption between 200-600 nm. The support SiMCM-41 showed the absorption bands at about 210 and 260 nm, indicating the framework coordinated siliceous species. In case of $CuFe_2O_4$/MCM-41 and $CuFe_2O_4$/mesosilicalite, the spectra showed a weak absorption below 230 nm and a strong and broad absorption between 240-800 nm. The peaks of $CuFe_2O_4$/MCM-41 and $CuFe_2O_4$/mesosilicalite correlate with cubic spinel exhibits tetrahedral (215 nm) and octahedral (440-700 nm) crystalline coordination sites [Najmoddin, N., et. al., Microporous Mesoporous Mater. 2014, 190, 346-355]. The presence of such peak absorption indicates the dispersion and integrated spinel ferrites over both supports. In the case of the mesosilicalite support, an enhanced intense broad peak shows the presence of higher crystalline mixed phase of oxides due to octahedral coordinated spinel species compared to the MCM-41 support (see FIG. 3). This can be attributed mainly due to presence of micropores, which tends to accommodate spinel species at the external surface of mesosilicalite. After loading of curcumin and cisplatin, the absorption maximum increases significantly over both $CuFe_2O_4$/Mesosilicalite and $CuFe_2O_4$/MCM-41 nanocomposites. However, in case with $CuFe_2O_4$/mesosilicalite/curcumin, a two band abortion at about 400 nm and 500 nm clearly indicates the presence of distributed curcumin and Pt species. However, with $CuFe_2O_4$/MCM-41/curcumin, a broadness of absorption peak indicates cohabitation of curcumin and Pt species over MCM-41. Such increase in homogenous expansion behavior clearly indicates the composite formation over mesoporous MCM-41 support than with mesosilicalite.

Figure 4:
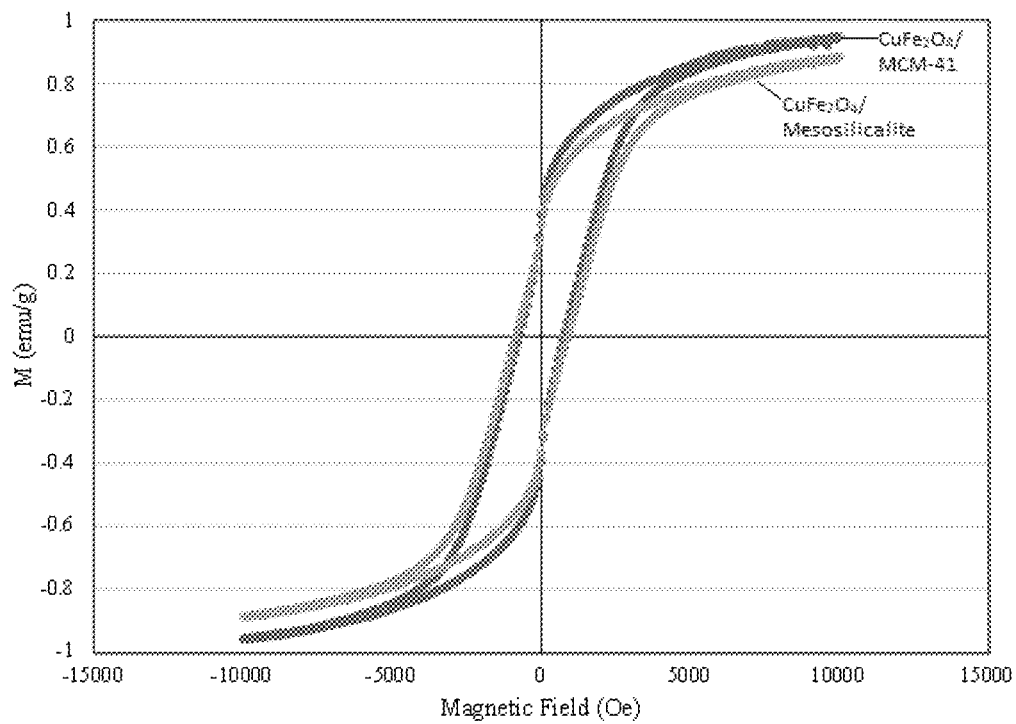
FIG. 4 shows vibrating sample magnetometer analysis of $CuFe_2O_4$/MCM-41 and $CuFe_2O_4$/Mesosilicalite.

The magnetic characteristics and saturation value of $CuFe_2O_4$/MCM-41 and $CuFe_2O_4$/Mesosilicalite nanocomposites were analyzed by vibrating sample magnetometer at room temperature (FIG. 4). A distribution of cations at different coordination sites of A and B characterize the magnetic property. $CuFe_2O_4$/MCM-41 and $CuFe_2O_4$/Mesosilicalite showed ferromagnetic property with saturation magnetization value of about 0.9 emu/g. The saturation magnetization value was reported to be related to the magnetic phase concentration. Fe loaded on high surface area MCM-41 was reported to exhibit magnetization of 3.86 emu/g [Kiatphuengporn, S., et. al., Chem. Engg. J. 2016, 306, 866-875]. In a previous study, spinel impregnation over spherical silica with lower surface area of 178 m²/g was found to exhibit similar ferromagnetism with magnetic value of about 7.6 emu/g [Jermy, B. R., et. al., J. Nanotechnol. 2019, 10, 2217-2228]. Further, it has been reported that superparamagnetic effect was due to anti parallel spins of $Fe^{3+}$ species in tetrahedral coordination site. From FIG. 4, it is clear that the support has been shown to influence the magnetic property. The loading of spinel over mesosilicalite support tends to generate different types of nanoclusters at the pore walls (as evidenced by increased pore diameter from 3.0 to 5.9 nm). The generation of small sized nanoclusters reported to generate super paramagnetic $Fe^{3+}$ ions, while larger nanoclusters generates ferromagnetic behavior [Cuello, N. I., et. al., Mater. Sci. Eng.; C 2017, 78, 674-681]. In line with the diffuse reflectance spectra, presence of tetrahedral and octahedral species over high surface area parent mesosilicalite and MCM-41 is proposed to lead the broad hysteresis structure characteristics of ferromagnetism. The observed reduction in saturation magnetization value is mainly attributed due to presence of siloxane layers on copper spinel ferrites.

Figure 5:
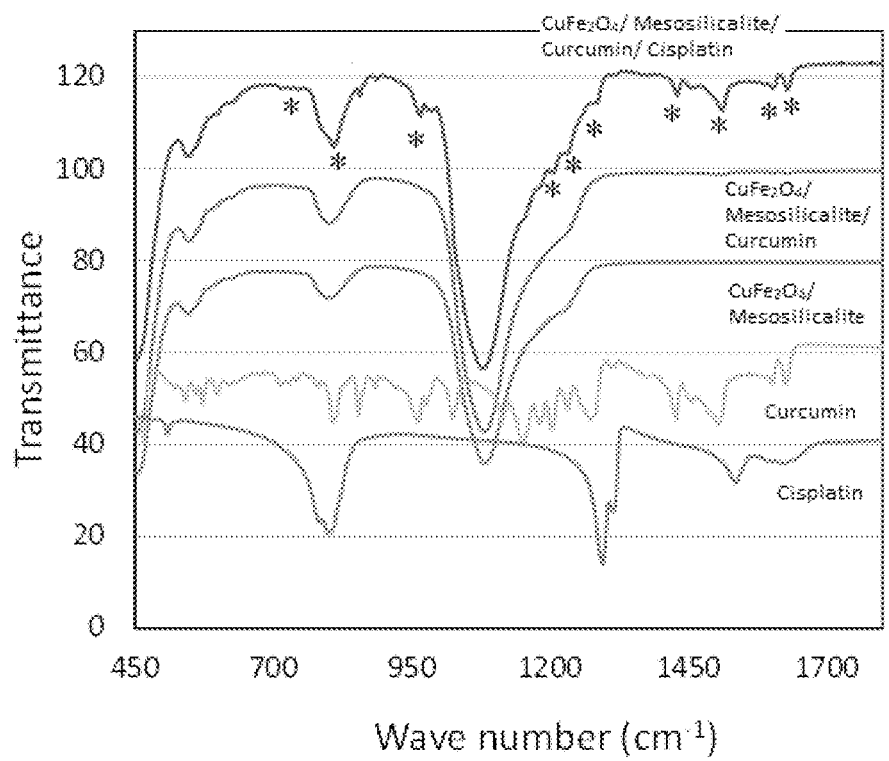
FIG. 5 shows FTIR spectra of Cisplatin, Curcumin, $CuFe_2O_4$/Mesosilicalite, $CuFe_2O_4$/Mesosilicalite/Curcumin, and $CuFe_2O_4$/Mesosilicalite/Curcumin/Cisplatin.

The FT-IR spectra of cisplatin, curcumin, $CuFe_2O_4$/mesosilicalite, $CuFe_2O_4$/mesosilicalite/curcumin and $CuFe_2O_4$/mesosilicalite/curcumin/cisplatin are shown in FIG. 5. Drug cisplatin showed a characteristic functional group related to NH group of platinum complex between 400-1800 cm$^{-1}$. A symmetric and asymmetric bending of NH 2 group was clearly observed between 1300-1600 cm$^{-1}$, while plane bending of cisplatin can be seen at about 800 cm-1. In the case of curcumin, the presence of carbonyl (C═O), carbon-carbon double bond (C═C), and methylene (CH 2) bending peaks are observed between 1625-1450 cm$^{-1}$. Both symmetric and asymmetric vibrations corresponding to ether bond (C—O—C) are observed between 1300-1000 cm$^{-1}$ [Bhandari, R., et. al., Mater. Sci. Eng. C. 2016, 67, 59-64]. A peak corresponding to the enolic OH group of curcumin appears clearly at about 960 cm$^{-1}$. In the case of $CuFe_2O_4$/mesosilicalite, a zeolitic peak indicating hybrid formation between mesoporous and microporous zeolite appears at about 550 cm$^{-1}$. In the case of $CuFe_2O_4$/mesosilicalite/curcumin (curcumin loading step 1), there was no distinct peaks of curcumin was observed. A significant reduction in hydroxyl group of enol indicates an effective interaction inside the mesosilicalite pores and curcumin. In the case of $CuFe_2O_4$/mesosilicalite/curcumin/cisplatin (cisplatin loading step 2) sample, the loading of cisplatin tends to shows the peaks of curcumin. It indicates that during cisplatin functionalization step, curcumin present inside the pores of mesosilicalite diffuse out and present at the external surface of mesosilicalite. The presence of peak at about 1023 cm$^{-1}$ indicates the C—O—C stretching of $C_6H_5$—O—$CH_3$ group [Mohan, P. R. K., et. al., Vib. Spectrosc. 2012, 62, 77-84]. Also, the presence of cisplatin peaks reveals an effective functionalization of drug at external surface of mesosilicalite.

Figure 6A:
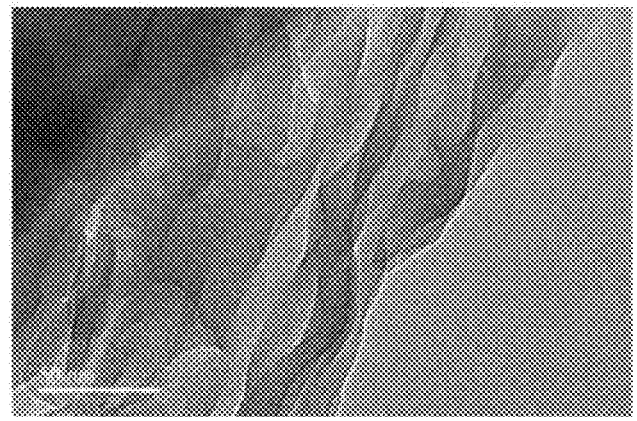
FIGS. 6A-6C are TEM microscopy images of the nanocomposites showing the hexagonal pore structure and curcumin layer.
Figure 6B:
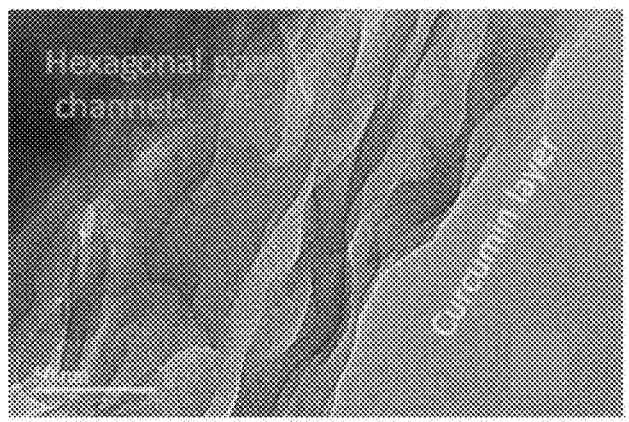
Figure 6C:
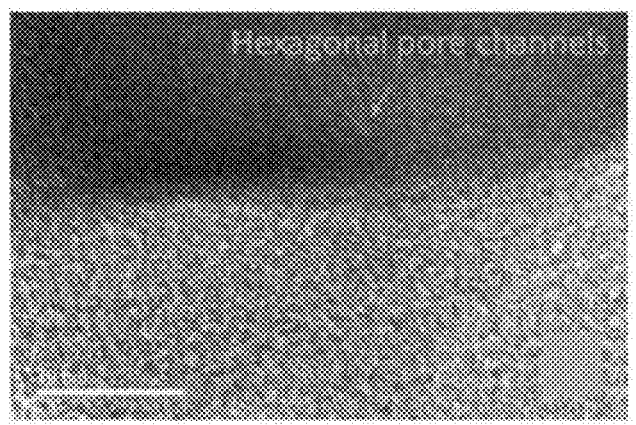

The morphological features of $CuFe_2O_4$/Mesosilicalite/Curcumin/Cisplatin were analyzed using transmission electron microscope at different scale bar of 50 nm and 10 nm (FIGS. 6A-6C). The images showed the presence of curcumin at the external surface of MCM-41, where uniformly layered hexagonal pore channels coexisting with curcumin. As detected in XRD and DRS-UV analysis, though the active spinel metal components were not readily distinguishable in TEM analysis, the migration of curcumin can be clearly observed as a surface coating at the external surface of mesosilicalite.

Figure 7:
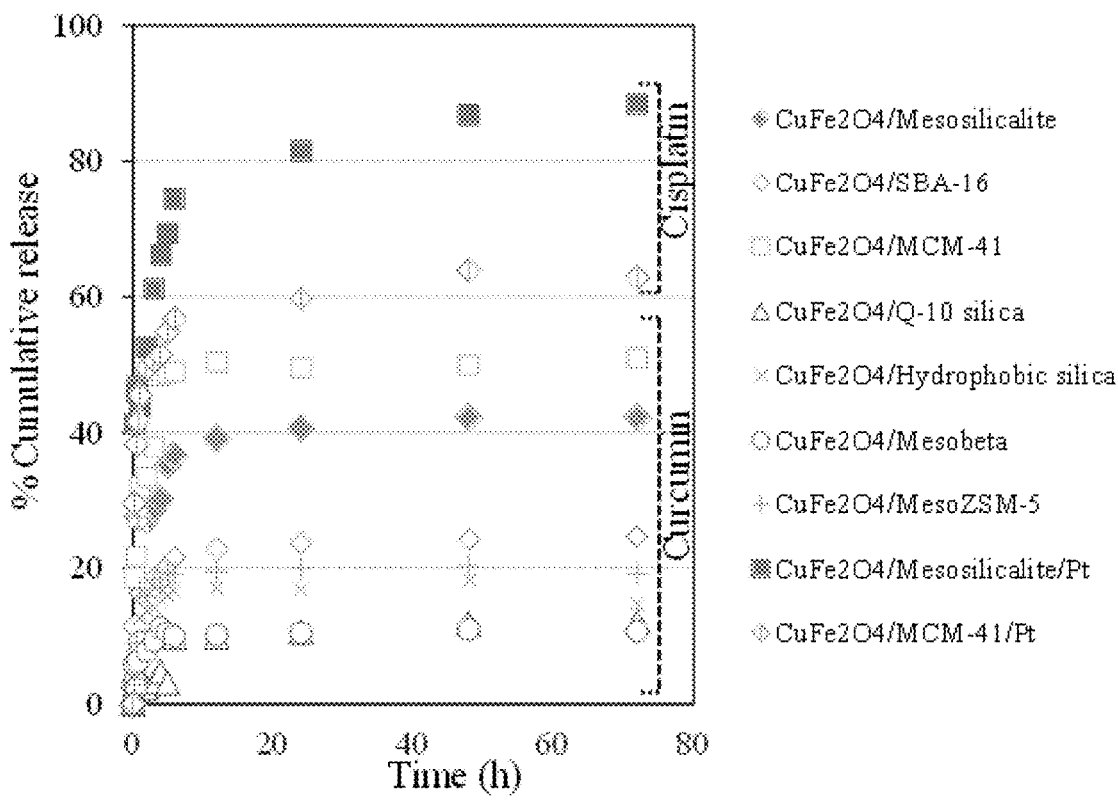
FIG. 7 shows drug (Curcumin, cisplatin) delivery over $CuFe_2O_4$ impregnated on different structured nanoporous materials at pH 5.6.

The release of curcumin over $CuFe_2O_4$ impregnated on different structured nanoporous mesosilicalite (hexagonal micro/mesopore), SBA-16 (cubic), MCM-41 (hexagonal mesopore), Q-10 (large pore), hydrophobic silica, mesobeta (BEA large pore) and mesoZSM-5 (MFI) are studied under acidic pH (pH 5.6) condition for 72 h (see FIG. 7). The percentage cumulative release profile of curcumin over hexagonal shaped silica (MCM-41 and mesosilicalite) was found to be superior of about 40-50% compared to cubic shaped SBA-16. $CuFe_2O_4$/SBA-16, which contains a 3D pore architecture showed a release of about 25% for 72 h. This indicates the ink shaped pores of SBA-16 (about 3.3 nm) are slightly restricted with spinel ferrite impregnation but showed a sustained release behavior with respect to curcumin. MesoZSM-5 with MFI structure consisting of sinusoidal pores of about 0.56 nm and spherical silica with hydrophobic character showed a release ability of 20%. Q-10 silica with pore size of about 18 nm and mesobeta with medium pore size of 3 nm showed comparatively a less curcumin release of 10%. The release trend shows the structured silica with different pore shapes profoundly affects the release of curcumin. For quick release, hexagonal shaped channel pores of MCM-41 and mesosilicalite can be more readily utilized than cubic shaped pores of SBA-16 and aluminosilicates. Based on the present requirement, cisplatin was loaded on curcumin/$CuFe_2O_4$/mesosilicalite and curcumin/$CuFe_2O_4$/MCM-41. The presence of micro and mesopores of mesosilicalite was found to favor the high release of cisplatin (88% for 72 h), while mesopores of MCM-41 showed a release of about 63% for 72 h. This suggest that cisplatin tends to functionalize on the external micropores of mesosilicalite, while MCM-41 is able to accommodate the cisplatin inside the mesopores. For different structured mesoporous nanocarriers, data analysis was done using Prism 8 software and SPSS software version 20.0 (Tables 2-5).

TABLE 3

Curcumin release over different $CuFe_2O_4$/structured silica based nanoformulations (One way ANOVA)

| | Sum of Squares | df | Mean Square | F | Sig. |
|---|---|---|---|---|---|
| Between Groups | 16267.638 | 7 | 2323.948 | 23.709 | .000 |
| Within Groups | 9312.051 | 95 | 98.022 | | |
| Total | 25579.689 | 102 | | | |

TABLE 4

Post Hoc tests for mean difference in Curcumin release among different $CuFe_2O_4$/structured silica based nanoformulations

| Comparision of $CuFe_2O_4$/structured silica based nanoformulations | | Mean Difference | Standard Error | Significance ($p < 0.05$) |
|---|---|---|---|---|
| $CuFe_2O_4$/MCM-41 | 7 | 23.44 | 3.963 | 0.000* |
| 1 | 7 | 12.85 | 3.883 | 0.008* |
| 2 | 7 | 0.08 | 3.883 | 1.000 |
| 3 | 7 | 22.69 | 3.883 | 0.000* |
| 4 | 7 | 10.85 | 3.883 | 0.036* |
| 5 | 7 | 4.08 | 3.883 | 0.829 |
| 6 | 7 | 8.54 | 3.883 | 0.148 |

*Significant at 0.05 level
1-Curcumin/$CuFe_2O_4$/Mesosilicalite,
2-Curcumin/$CuFe_2O_4$/SBA-16,
3-Curcumin/$CuFe_2O_4$/MCM-41,
4-Curcumin/$CuFe_2O_4$/Q-10 Silica,
5-Curcumin/$CuFe_2O_4$/Hydrophobic silica,
6-Curcumin/$CuFe_2O_4$/Mesobeta and
7-Curcumin/$CuFe_2O_4$/MesoZSM-5

TABLE 2

Descriptive Statistics of Curcumin Release over different $CuFe_2O_4$/structured silica based nonoformulations

| Samples | N | Mean | Std. Deviation | Std. Error | 95% Confidence Interval for Mean | | Minimum | Maximum |
|---|---|---|---|---|---|---|---|---|
| | | | | | Lower Bound | Upper Bound | | |
| $CuFe_2O_4$/MCM-41 | 12 | 40.67 | 19.616 | 5.663 | 28.20 | 53.13 | 19 | 74 |
| 1 | 13 | 30.08 | 11.996 | 3.327 | 22.83 | 37.33 | 2 | 42 |
| 2 | 13 | 17.15 | 7.548 | 2.093 | 12.59 | 21.72 | 3 | 25 |
| 3 | 13 | 39.92 | 11.807 | 3.275 | 32.79 | 47.06 | 19 | 51 |
| 4 | 13 | 6.38 | 3.948 | 1.095 | 4.00 | 8.77 | 2 | 12 |
| 5 | 13 | 13.15 | 5.080 | 1.409 | 10.08 | 16.22 | 1 | 18 |
| 6 | 13 | 8.69 | 2.626 | .728 | 7.11 | 10.28 | 2 | 11 |
| 7 | 13 | 17.23 | 5.890 | 1.634 | 13.67 | 20.79 | 3 | 28 |
| Total | 103 | 21.48 | 15.836 | 1.560 | 18.38 | 24.57 | 1 | 74 |

1 - Curcumin/$CuFe_2O_4$/Mesosilicalite,
2 - Curcumin/$CuFe_2O_4$/SBA-16,
3 - Curcumin/$CuFe_2O_4$/MCM-41,
4 - Curcumin/$CuFe_2O_4$/Q-10 Silica,
5 - Curcumin/$CuFe_2O_4$/Hydrophobic silica,
6 - Curcumin/$CuFe_2O_4$/Mesobeta and
7 - Curcumin/$CuFe_2O_4$/MesoZSM-5

TABLE 5

Pearson correlation of Curcumin release over different $CuFe_2O_4$/structured based nanoformulations

| $CuFe_2O_4$/MCM-41 | | 1 | 2 | 3 | 4 | 5 | 6 | 7 |
|---|---|---|---|---|---|---|---|---|
| $CuFe_2O_4$/MCM-41 | 1 | | | | | | | |
| 1 | 0.341 | 1 | | | | | | |
| 2 | 0.515 | 0.937** | 1 | | | | | |
| 3 | 0.537 | 0.914** | 0.943** | 1 | | | | |
| 4 | 0.744** | 0.599* | 0.644* | 0.666* | 1 | | | |
| 5 | 0.375 | 0.932** | 0.956** | 0.917** | 0.504 | 1 | | |
| 6 | 0.455 | 0.810** | 0.898** | 0.881** | 0.535 | 0.828** | 1 | |
| 7 | 0.157 | 0.777** | 0.541 | 0.538 | 0.146 | 0.617* | 0.463 | 1 |

**Correlation is significant at the 0.01 level (2-tailed).
*Correlation is significant at the 0.05 level (2-tailed).
1 - Curcumin/$CuFe_2O_4$/Mesosilicalite,
2 - Curcumin/$CuFe_2O_4$/SBA-16,
3 - Curcumin/$CuFe_2O_4$/MCM-41,
4 - Curcumin/$CuFe_2O_4$/Q-10 Silica,
5 - Curcumin/$CuFe_2O_4$/Hydrophobic silica,
6 - Curcumin/$CuFe_2O_4$/Mesobeta and
7 - Curcumin/$CuFe_2O_4$/MesoZSM-5

Table 2 shows the mean and standard deviation of curcumin drug release at pH 5.6. $CuFe_2O_4$/MCM-41 showed a high mean score of 40.67, whereas $CuFe_2O_4$/Q-10 Silica/Curcumin demonstrated a low mean score of 6.38. The maximum score of curcumin drug release at pH 5.6 was observed in $CuFe_2O_4$/MCM-41/Curcumin and $CuFe_2O_4$/MesoZSM-5/Curcumin, however the minimum curcumin release was observed in $CuFe_2O_4$/Hydrophobic silica/Curcumin. From Table 3, the results showed that there is significant difference between the groups with respect to curcumin release at pH 5.6 ($p<0.05$).

As significant difference was found, Scheffe's post hoc test was used to determine the significant difference between two groups at the same time. It is observed that the mean difference in the curcumin release between the groups such as $CuFe_2O_4$/MCM-41 and $CuFe_2O_4$/MesoZSM-5; $CuFe_2O_4$/Mesosilicalite and $CuFe_2O_4$/MesoZSM-5; $CuFe_2O_4$/MCM-41 and $CuFe_2O_4$/MesoZSM-5; $CuFe_2O_4$/Q-10 silica and $CuFe_2O_4$/MesoZSM-5 was found to be significant ($p<0.05$). However, no significant mean difference was observed between the groups such as $CuFe_2O_4$/SBA-16 and $CuFe_2O_4$/MesoZSM-5; $CuFe_2O_4$/Hydrophobic silica and $CuFe_2O_4$/MesoZSM-5; $CuFe_2O_4$/MesoZSM-5 and $CuFe_2O_4$/MesoZSM-5 with respect to the curcumin release ($p>0.05$). Notably, $CuFe_2O_4$/MCM-41 showed a high mean difference score of curcumin release (40.67) with $CuFe_2O_4$/MesoZSM-5 when compared other $CuFe_2O_4$/structured silica based nanoformulations (See Table 4).

Using Pearson correlation, it was inferred that $CuFe_2O_4$/MCM-41 has a significant strong and positive correlation with only $CuFe_2O_4$/Q-10 silica/Curcumin ($p<0.01$). The formulation variable $CuFe_2O_4$/Mesosilicalite/Curcumin showed a significant strong and positive correlation with the variables such as $CuFe_2O_4$/SBA-16/Curcumin, $CuFe_2O_4$/MCM-41/Curcumin, $CuFe_2O_4$/Hydrophobic silica/Curcumin, $CuFe_2O_4$/MesoZSM-5/Curcumin, and $CuFe_2O_4$/Mesobeta/Curcumin ($p<0.01$). Similarly, $CuFe_2O_4$/SBA-16/Curcumin described a significant strong and positive correlation with the formulation variables such as $CuFe_2O_4$/MCM-41/Curcumin, $CuFe_2O_4$/Hydrophobic silica/Curcumin, and $CuFe_2O_4$/Me sob eta/Curcumin ($p<0.01$). Further, $CuFe_2O_4$/MCM-41/Curcumin showed a significant strong and positive correlation with $CuFe_2O_4$/Hydrophobic silica/Curcumin and $CuFe_2O_4$/Mesobeta/Curcumin ($p<0.01$). A significant strong and positive relationship was observed between $CuFe_2O_4$/Hydrophobic silica/Curcumin and $CuFe_2O_4$/Mesobeta/Curcumin ($p<0.01$) (Table 5). On the other hand, $CuFe_2O_4$/Q-10 silica/Curcumin described a significant moderate and positive correlation with $CuFe_2O_4$/Mesosilicalite/Curcumin, $CuFe_2O_4$/SBA-16/Curcumin, and $CuFe_2O_4$/MCM-41/Curcumin ($p<0.05$). A significant moderate and positive correlation was also observed between $CuFe_2O_4$/MesoZSM-5/Curcumin and $CuFe_2O_4$/Hydrophobic silica/Curcumin ($p<0.05$) (See Table 5).

Figure 8A:
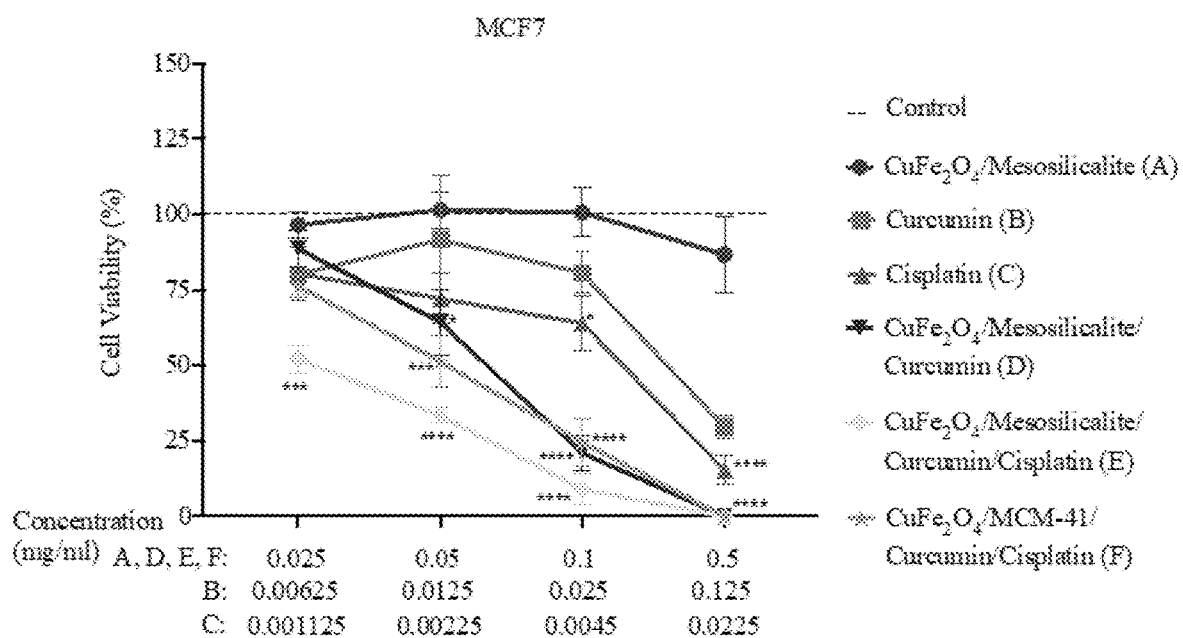
FIGS. 8A-8B are plots of cell survivability showing cytotoxic effects on various cell lines using MTT assay, where
Figure 8B:
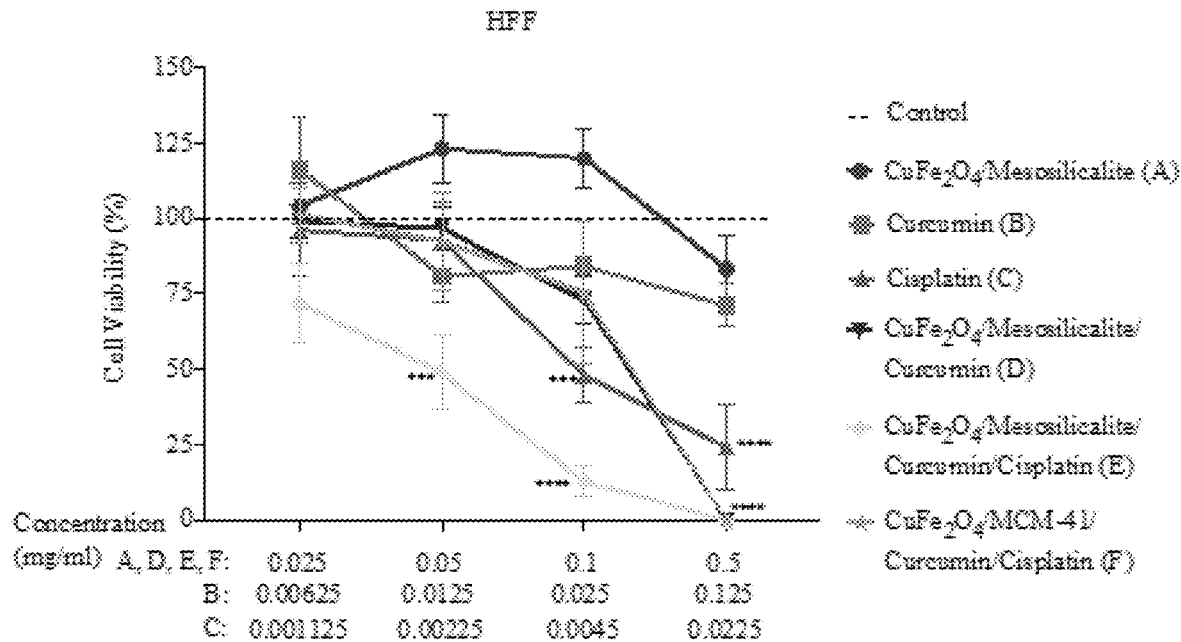
Figure 9A:
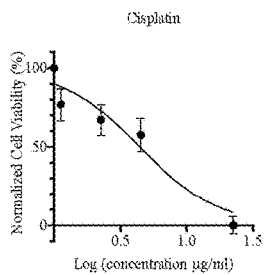
FIGS. 9A-9H are plots of cell survivability showing the dose-dependent survivability for cisplatin, $CuFe_2O_4$/Mesosilicalite/curcumin, $CuFe_2O_4$/Mesosilicalite/curcumin/cisplatin, and $CuFe_2O_4$/MCM-41/curcumin/cisplatin, where
Figure 9B:
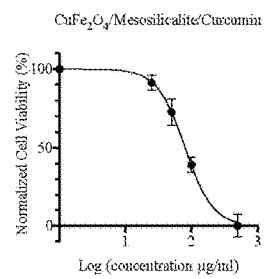
Figure 9C:
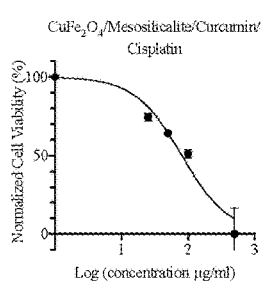
Figure 9D:
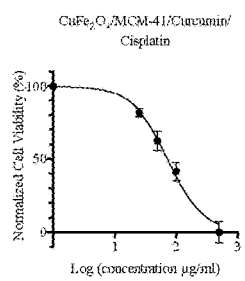
Figure 9E:
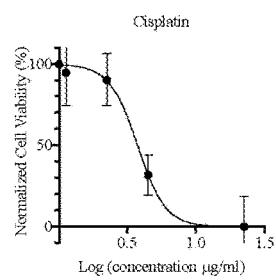
Figure 9F:
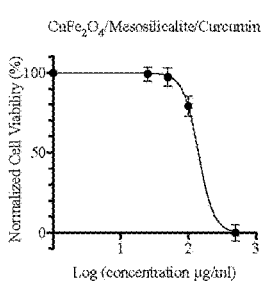
Figure 9G:
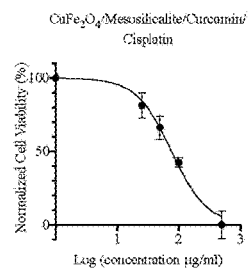
Figure 9H:
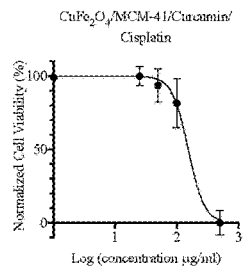

To test the efficiency of the nanocomposites as potential chemotherapeutic agents, their effects on the cell viability of MCF7 (breast cancer) and HFF (human foreskin fibroblast) cell lines were investigated. The cell viability assay, MTT, was performed after 48 h of treatment with the following conditions: $CuFe_2O_4$/Mesosilicalite, Curcumin, Cisplatin, $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin nanocomposites. The results are shown in FIG. 8A for MCF7 cell line and in FIG. 8B for HFF cell line. Treatment concentrations of $CuFe_2O_4$/Mesosilicalite, $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin nanocomposites were: 0.025, 0.05, 0.1, and 0.5 mg/ml. While treatment concentrations for curcumin were: 0.00625, 0.0125, 0.025 and 0.125 mg/ml and that for the cisplatin group: 0.00225, 0.0045, and 0.0225 mg/ml. As detailed in the Materials and Methods section, treatment concentrations of curcumin and cisplatin were adjusted to reflect the actual concentration adsorbed onto the mesosilicalite nanocomposites.

The results were analyzed by comparing data from the treated cells with the control group (untreated cells). Cells treated with $CuFe_2O_4$/Mesosilicalite nanocomposites had no effect on either MCF7 or HFF cells suggesting that the $CuFe_2O_4$/Mesosilicalite nanocarrier did not interfere with cell viability. Pure curcumin reduced cell viability only at the highest concentration in MCF7; however, it minimally reduced the cell viability in HFF cell lines. As anticipated, pure cisplatin resulted in a reduction in cell viability in both MCF7 and HFF cell lines. Furthermore, cells that were treated with the nanocomposites $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin all resulted in a significant reduction in cell viability in a dose-dependent manner (see FIGS. 8A-8B).

Upon close investigation at the third dose of treatment in MCF7 cells, the pure curcumin reduced cell viability to 80.71%, while the nanocomposites that were coated with curcumin either with or without cisplatin significantly reduced the cell viability to 20.98% (group D in FIG. 8A), and 8.96% (group E in FIG. 8A). In contrast, using the same dose on the non-cancerous cell line HFF, the pure curcumin reduced cell viability to 84.12%, whereas the nanocomposites that were coated with curcumin did not result in a significant reduction in cell viability (72.88%; group D in FIG. 8B). Whereas HFF treated with nanocomposites that were coated with curcumin and functionalized with cisplatin resulted in a significant reduction in cell viability of 12.93% (group E in FIG. 8B). Interestingly, the $CuFe_2O_4$/MCM-41/Curcumin/Cisplatin nanocomposite resulted in a significant reduction of cell viability of 24.44% in MCF7 (group F in FIG. 8A), and an insignificant reduction in viability of 75.53% in HFF (group F in FIG. 8B). Using a drug combination of cisplatin and curcumin nanocomposites will increase the cumulative cytotoxic effects of both compounds, solve the problem of cisplatin drug resistance in tumors, and increase the bioavailability of curcumin. The $CuFe_2O_4$/Mesosilicalite/Curcumin/Cisplatin nanocomposite had a stronger effect even at lower concentrations on both cell lines. However, using the MCM-41/mesosilicalite in the cisplatin/curcumin nanocomposite had a significant effect on MCF7, while having a minimal effect on HFF. These results suggest that using MCM-41 with a cisplatin/curcumin drug combination has the potential of affecting cancerous cells while sparing normal ones.

To calculate the EC50 of treatment conditions, the data from release profiles (see FIGS. 9A-9H) was used to extrapolate the line equation and calculate the EC50. The calculated EC50 values are compiled in Table 6 for MCF7 cell line and Table 7 for HFF cell line. Treatment with cisplatin resulted in an EC50 of 4.425 and 3.763 µg/ml in MCF7 and HFF, respectively. Coating the $CuFe_2O_4$/Mesosilicalite with curcumin resulted in an EC50 of 80.2 µg/ml in MCF7 and 141.0 mg/ml in HFF. Moreover, functionalizing the $CuFe_2O_4$/Mesosilicalite with curcumin and cisplatin resulted in an EC50 of 81.23 µg/ml in MCF7 and 76.83 µg/ml in HFF. However, functionalizing curcumin and cisplatin onto $CuFe_2O_4$/MCM-41 nanocomposite resulted in an EC50 of 72.51 µg/ml in MCF7 and 154.2 mg/ml in HFF. These results show that while using the mesosilicalite resulted in a similar EC50, using the MCM-41 support resulted in a fold difference in EC50 values between MCF7 and HFF. When comparing between the nanocomposites, these results show that both $CuFe_2O_4$/Mesosilicalite/Curcumin/Cisplatin and $CuFe_2O_4$/MCM-41/Curcumin/Cisplatin nanocomposites are potential novel chemotherapeutic options. However, the results show that $CuFe_2O_4$/MCM-41/Curcumin/Cisplatin may be a better candidate due to the wider difference in EC50 (a fold change) between cancerous and non-cancerous cell line.

TABLE 6

Calculated EC50 values for the nanocarrier against MCF-7 cell line.

| Drug Group | Log $EC_{50}$ Value | $EC_{50}$ Value (µg/mL) | $R^2$ |
| --- | --- | --- | --- |
| Cisplatin | 0.6459 | 4.425 | 0.7444 |
| $CuFe_2O_4$/Mesosilicalite/Curcumin | 1.904 | 80.20 | 0.9106 |
| $CuFe_2O_4$/Mesosilicalite/Curcumin/Cisplatin | 1.910 | 81.23 | 0.7990 |
| $CuFe_2O_4$/MCM-41/Curcumin/Cisplatin | 1.860 | 72.51 | 0.9067 |

TABLE 7

Calculated EC50 values for the nanocarrier against HFF cell line

| Drug Group | Log $EC_{50}$ Value | $EC_{50}$ Value (µg/mL) | $R^2$ |
| --- | --- | --- | --- |
| Cisplatin | 0.5755 | 3.763 | 0.6306 |
| $CuFe_2O_4$/Mesosilicalite/Curcumin | 2.149 | 141.0 | 0.9415 |
| $CuFe_2O_4$/Mesosilicalite/Curcumin/Cisplatin | 1.886 | 76.83 | 0.8560 |
| $CuFe_2O_4$/MCM-41/Curcumin/Cisplatin | 2.188 | 154.2 | 1.7742 |

Figure 10:
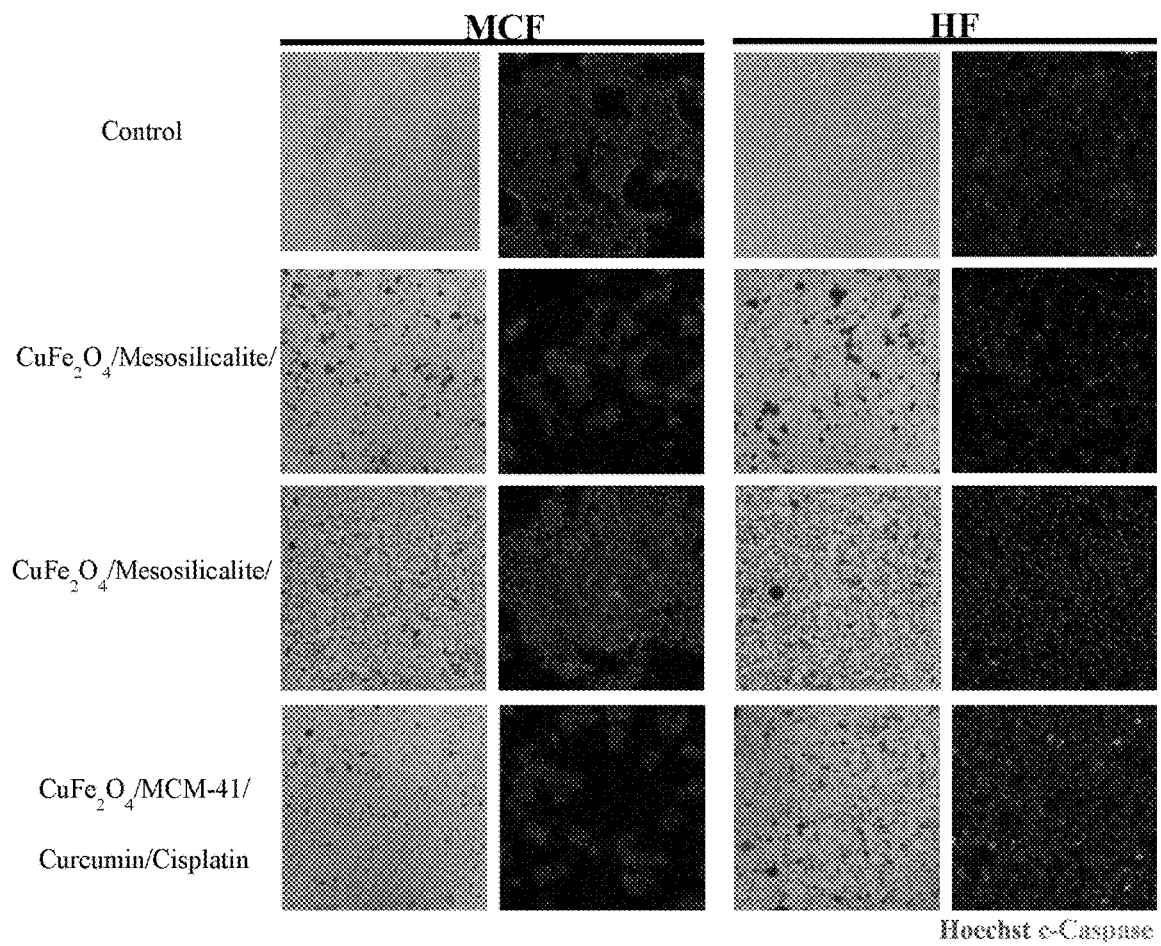
FIG. 10 shows light microscopy and immunofluorescence images showing the apoptotic effect of different treatment conditions on MCF7 and HFF cells were treated with $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin at a concentration of 0.5 mg/ml for 48 h.
Figure 11:
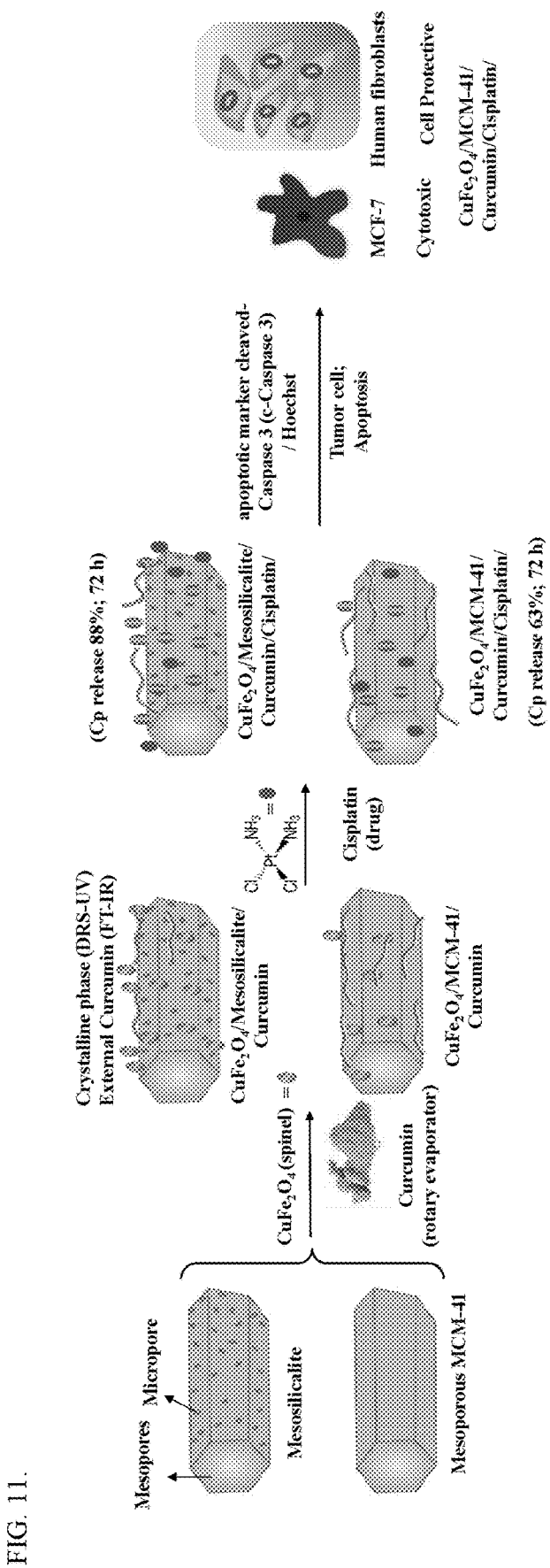
FIG. 11 is a depiction of the structure of the $CuFe_2O_4$/Mesosilicalite/curcumin/cisplatin and $CuFe_2O_4$/MCM-41/curcumin/cisplatin nanocomposites.

Further, the apoptotic effects of treating cells with $CuFe_2O_4$/Mesosilicalite/Curcumin, $CuFe_2O_4$/Mesosilicalite/Curcumin/Cisplatin, and $CuFe_2O_4$/MCM-41/Curcumin/Cisplatin nanocomposites were explored. Cells were viewed under light and fluorescent microscopes. For the latter, cells were stained with the apoptotic marker cleaved-Caspase 3 (c-Caspase 3), 10 and Hoechst, which is a nuclear marker. These images are presented in FIG. 10. The images clearly show cells stained (magenta) with c-Caspase 3, which is the activated form of the protein, after treatment with our nanocomposites for 48 h. These results suggest that the nanocomposites significantly reduce cell viability by activating apoptosis.

Curcumin has been extensively investigated as a chemotherapeutic agent in breast cancer, hepatocellular carcinoma, pancreatic cancer, gastric cancer, osteoclastoma, and bladder cancer [Li, W., et. al., Oncol Rep. 2017, 37, 3459-3466; Cao, F., et. al., Int J Clin Exp Pathol. 2015, 8(6), 6037-6045; and Zhang, L., et. al., Int J Oncol. 2018, 53, 515-526]. It has been found to activate INK pathway, induce the generation of reactive oxygen species (ROS), and subsequently apoptosis [Syng-Ai, C., et. al., Mol Cancer Ther. 2004, 3(9), 1101-1108; and Zhu, Y., & Bu, S., Evidence-Based Complementary and Alternative Medicine 2017, 1-13]. However, curcumin has some problems that hinder its full potential such as low solubility, low bioavailability, and rapid elimination from the body [Anand, P., et. al., Mol Pharm. 2007, 4(6), 807-818]. Research is being conducted to increase the bioavailability of curcumin. On the other hand, cisplatin is a well-established chemotherapeutic drug. Unfortunately, it is fraught with several issues such as drug resistance and systemic toxicity [Dasari, S., & Bernard Tchounwou, P., European J. Pharmacol. 2014, 740, 364-378]. The mechanism of action of cisplatin is by activating the INK pathway and inducing oxidative stress, DNA damage, and apoptosis. However, cisplatin will also result in increased levels of Glutathione S transferase (GST), resulting in a reduction in ROS, and resistance to cisplatin. Therefore, a combination treatment of cisplatin and curcumin, which increases ROS, might augment the cytotoxic effect and prevent cisplatin-related drug resistance [Townsend, D. M., & Tew, K. D., Oncogene 2003, 22, 7369-7375]. Moreover, these results show that the structural framework of silica had a significant effect on the cytotoxic effectiveness of nanocomposites. In a previous publication by the inventors of the current disclosure, cisplatin-functionalized cubic spinel $CuFe_2O_4$ loaded on monodispersed spherical hydrophilic silica (HYPS) nanoparticles was tested on MCF7 breast cancer cells [Jermy, B. R., et. al., J. Nanotechnol. 2019, 10, 2217-2228]. In the present disclosure, two nanoformulations using silicate materials having hexagonally shaped pores: a) the mesosilicalite with zeolite (strong) framework, and b) the MCM-41 with amorphous (weak) framework were used. Both of which were coated with curcumin and functionalized with cisplatin. While the EC50 of the previous spherical shaped silica nanoformulation was equal to 180.89 µg/ml (See Jermy, B. R., et. al., J. Nanotechnol. 2019, 10, 2217-2228) the present hexagonal shaped silica nanocomposites had EC50 values of 81.23 µg/ml (mesosilicalite) and 72.51 µg/ml (MCM-41). These results clearly indicate that changing the structural framework from spherical to hexagonally shaped silica increased the chemotherapeutic efficiency and reduced the EC50 values. This improved effectiveness marks a significant improvement brought about by the change in the silicate matrix.

The invention claimed is:

1. A method for treating a breast cancer in a subject in need of therapy, comprising:
administering to the subject a pharmaceutical composition comprising a nanomedicinal composition,
wherein the nanomedicinal composition comprises:
a nanocarrier comprising:
mesosilicalite; and
particles of a magnetic ferrite of formula $MFe_2O_4$ disposed in the pores of the mesosilicalite, where M is Cu; and
a pharmaceutical agent mixture comprising cisplatin and curcumin disposed in the pores and/or on a surface of the nanocarrier;
wherein the nanocarrier has a BET surface area of 70 $m^2/g$ and an average pore volume of 0.1 $cm^3/u$,
wherein the nanomedicinal composition releases 88% of the cisplatin and 40-50% of the curcumin over 72 hours in a solution with a pH of 5.6.

2. The method of claim 1, wherein the mesosilicalite is in the form of particles having a mean particle size of 25 to 500 nm.

3. The method of claim 1, wherein the magnetic ferrite is present in the nonmedicinal composition an amount of 15 to 45 wt % based on a total weight of the nanocarrier.

4. The method of claim 1, wherein the magnetic ferrite has a mean particle size of 5 to 50 nm.

5. The method of claim 1, wherein the pharmaceutical agent mixture further comprises at least one selected from the group consisting of carboplatin and oxaliplatin.

6. The method of claim 1, wherein the pharmaceutical agent further comprises tamoxifen.

7. The method of claim 1, wherein the nanomedicinal composition further comprises at least one selected from the group consisting of quercetin, rutin, coenzyme Q10, and gallic acid.

8. The method of claim 1, wherein a weight ratio of the curcumin to the cisplatin is 1:1 to 10:1 in the nonmedicinal composition.

9. The method of claim 1, wherein the pharmaceutical agent mixture is present in the nanomedicinal composition in an amount of 5 to 50 wt %, based on a total weight of nanomedicinal composition.

10. The method of claim 1, further comprising exposing the subject to an alternating magnetic field after the administering, thereby raising the temperature of the nanomedicinal composition.

* * * * *